US011873342B2

United States Patent
Li et al.

(10) Patent No.: US 11,873,342 B2
(45) Date of Patent: Jan. 16, 2024

(54) ANTI-CCR8 MONOCLONAL ANTIBODIES AND USES THEREOF

(71) Applicant: LaNova Medicines Limited, Shanghai (CN)

(72) Inventors: Runsheng Li, Shanghai (CN); Wentao Huang, Shanghai (CN)

(73) Assignee: LaNova Medicines Limited, Shanghai (CN)

(*) Notice: Subject to any disclaimer, the term of this patent is extended or adjusted under 35 U.S.C. 154(b) by 0 days.

(21) Appl. No.: 17/685,036

(22) Filed: Mar. 2, 2022

(65) Prior Publication Data

US 2022/0195057 A1 Jun. 23, 2022

Related U.S. Application Data

(63) Continuation of application No. PCT/CN2021/122994, filed on Oct. 11, 2021.

(30) Foreign Application Priority Data

Oct. 16, 2020 (WO) ............... PCT/CN2020/121494

(51) Int. Cl.
  *C07K 16/28* (2006.01)
  *A61P 35/00* (2006.01)
  *A61K 39/00* (2006.01)

(52) U.S. Cl.
  CPC .......... *C07K 16/2866* (2013.01); *A61P 35/00* (2018.01); *A61K 2039/505* (2013.01); *C07K 2317/24* (2013.01); *C07K 2317/41* (2013.01); *C07K 2317/565* (2013.01); *C07K 2317/732* (2013.01); *C07K 2317/92* (2013.01)

(58) Field of Classification Search
  CPC .............................. C07K 16/00; A61K 39/541
  See application file for complete search history.

(56) References Cited

U.S. PATENT DOCUMENTS

| | | |
|---|---|---|
| 10,087,259 B1 | 10/2018 | Rudensky et al. |
| 10,550,191 B2 | 2/2020 | Yoshida et al. |
| 2011/0059107 A1 | 3/2011 | Allison et al. |
| 2020/0222463 A1 | 7/2020 | Yoshida et al. |
| 2021/0047421 A1 | 2/2021 | Yoshida et al. |
| 2021/0238292 A1 | 8/2021 | Holland et al. |
| 2021/0277129 A1 | 9/2021 | McGrath et al. |

FOREIGN PATENT DOCUMENTS

| | | |
|---|---|---|
| CN | 102782148 A | 11/2012 |
| CN | 110835371 A | 2/2020 |
| CN | 110835374 A | 2/2020 |
| WO | 1999006561 A2 | 2/1999 |
| WO | 2012172341 A2 | 12/2012 |
| WO | 2020138489 A1 | 7/2020 |
| WO | 2020177627 A1 | 9/2020 |
| WO | 2021152186 A2 | 8/2021 |
| WO | 2021178749 A2 | 9/2021 |
| WO | 2021194942 A1 | 9/2021 |

OTHER PUBLICATIONS

Bendig M. M. (Methods: A Companion to Methods in Enzymology, 1995; 8:83-93) (Year: 1995).*
Portolano (The Journal of Immunology, vol. 150, No. 3, p. 880-887, 1993) (Year: 1993).*
Beiboer (J. Mol. Biol. (2000) 296:833-849) (Year: 2000).*
Rudikoff et al. (Proceedings of the National Academy of Sciences USA, vol. 79, p. 1979-1983, 1982) (Year: 1982).*
Paul (Fundamental Immunology, 3rd Edition, 1993, pp. 292-295) (Year: 1993).*

* cited by examiner

Primary Examiner — Michael Allen

(57) ABSTRACT

Provided are antibodies or fragment thereof having binding specificity to the human chemokine (C—C motif) receptor 8 (CCR8) protein. These antibodies are capable of binding to CCR8 at high affinity and can mediate antibody-dependent cellular cytotoxicity (ADCC).

9 Claims, 13 Drawing Sheets

Specification includes a Sequence Listing.

ANTI-CCR8 MONOCLONAL ANTIBODIES AND USES THEREOF

CROSS REFERENCE TO RELATED APPLICATIONS

The present application is a continuation of International Application No. PCT/CN2021/122994, filed Oct. 11, 2021, which claims priority to PCT/CN2020/121494, filed Oct. 16, 2020, the content of each of which is incorporated herein by reference in its entirety in the present disclosure.

SEQUENCE LISTING

The instant application contains a Sequence Listing which has been submitted in ASCII format via EFS-Web and is hereby incorporated by reference in its entirety. Said ASCII copy, created on Aug. 22, 2023, is named 322175US_Seq_listing_ST25.txt and is 38,972 bytes in size.

BACKGROUND

Chemokine (C—C motif) receptor 8 (CCR8) is a member of the beta chemokine receptor family, and is a seven transmembrane protein similar to G protein-coupled receptors. Chemokines and their receptors are important for the migration of various cell types into the inflammatory sites. This receptor protein preferentially expresses in the thymus. The ligand of the CCR8 is CCL1. CCL8 also functions as a CCR8 agonist.

CCR8 is expressed principally on regulatory T cells (Treg) and is important for CCR8$^+$ Treg-mediated immunosuppression. Recent studies have demonstrated that CCR8 is uniquely upregulated in human tumor-resident Tregs of cancer patients. It was also demonstrated that CCR8$^+$ myeloid cells were expanded in patients with cancer.

Antibodies targeting CCR8 have been shown to significantly suppress tumor growth and improve long-term survival in animal models. This antitumor activity correlated with increased tumor specific T cells, and enhanced infiltration of CD4$^+$ and CD8$^+$ T cells. Treatment with the antibodies prevented induction and suppressive function of Tregs without affecting CD8$^+$ T cells. Targeting CCR8, therefore, is a promising cancer immunotherapy approach.

SUMMARY

Anti-CCR8 antibodies are discovered herein that have high binding affinity to the human CCR8 protein, and are efficient in mediating antibody-dependent cellular cytotoxicity (ADCC).

In one embodiment, an antibody or fragment thereof is provided, having binding specificity to a human chemokine (C—C motif) receptor 8 (CCR8) protein. The antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3. In one embodiment, the CDRH1 comprises the amino acid sequence of SEQ ID NO: 22, the CDRH2 comprises the amino acid sequence of SEQ ID NO: 23, the CDRH3 comprises the amino acid sequence of SEQ ID NO: 24, the CDRL1 comprises the amino acid sequence of SEQ ID NO: 25 or 28, the CDRL2 comprises the amino acid sequence of SEQ ID NO: 26, and the CDRL3 comprises the amino acid sequence of SEQ ID NO: 27.

In one embodiment, the CDRH1 comprises the amino acid sequence of SEQ ID NO: 35, the CDRH2 comprises the amino acid sequence of SEQ ID NO: 36, the CDRH3 comprises the amino acid sequence of SEQ ID NO: 37, the CDRL1 comprises the amino acid sequence of SEQ ID NO: 25 or 28, the CDRL2 comprises the amino acid sequence of SEQ ID NO: 26, and the CDRL3 comprises the amino acid sequence of SEQ ID NO: 27.

Also provided, in some embodiments, are compositions comprising the antibody or fragment thereof and a pharmaceutically acceptable carrier. In some embodiments, the composition further comprises a second antibody having specificity to a tumor antigen. In some embodiments, the second antibody is a tumor-opsonizing antibody.

Methods and uses for the treatment of diseases and conditions are also provided. In one embodiment, provided is a method of treating cancer in a patient in need thereof, comprising administering to the patient the antibody or fragment thereof of the present disclosure.

DETAILED DESCRIPTION

Definitions

Figure 1:
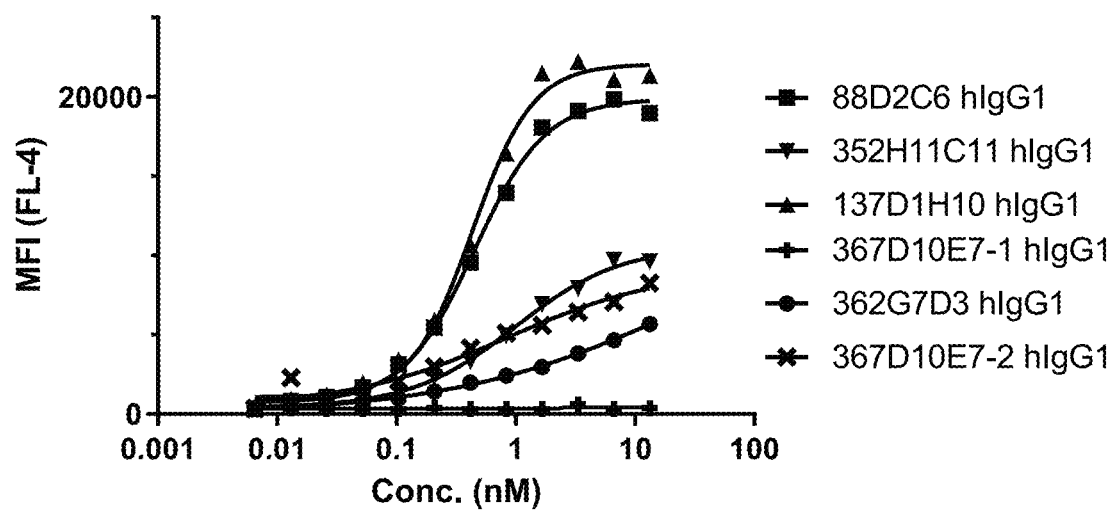
FIG. 1 shows the CCR8-binding affinity of the chimeric antibodies with murine VH/VL.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody. For example, an antibody fragment or antigen-binding fragment can be F(ab')$_2$, F(ab)$_2$, Fab', Fv, or scFv. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgG$_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three-dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
| --- | --- | --- |
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G (SEQ ID NO: 44), where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G (SEQ ID NO: 44), where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-CCR8 Antibodies

The present disclosure provides anti-CCR8 antibodies and fragments that have high affinity to the human CCR8 protein, are potent in mediating ADCC and ADCP, and showed potent in vivo tumor inhibitor efficacy. Interesting, when using an anti-CCR8 antibody (from WO2020138489) as a benchmark, the instantly disclosed antibodies exhibited no binding to non-CCR8-expressing cells, while the benchmark antibody bound to those control cells as well. The present antibodies, therefore, can be expected to have less undesired adverse effects in clinical uses. These antibodies, therefore, are suitable agents for treating various diseases featuring overexpressed CCR8, such as cancer.

In accordance with one embodiment of the present disclosure, therefore, provided are antibodies and antigen-binding fragments thereof that are able to bind to CCR8. Example antibodies include those murine ones listed in Table 1 (e.g., 137D1H10, 88D2C6, 89B6F8, 132H8E10, 10F11B2, 40H10F3, 53D6A9, 352H11C11, 362G7D3, 362H10A3, 367D10E7, 370D2C10), as well as humanized ones of Tables 2-3. Also included are those that include the same CDRs as illustrated herein. In some embodiments, the disclosed antibodies and fragments include those that bind to the same epitope as those illustrated here, and those that compete with the instantly disclosed in binding to CCR8.

In accordance with one embodiment of the present disclosure, provided is an antibody or fragment thereof that includes the heavy chain and light chain variable domains with the CDR regions disclosed herein, as well as their biological equivalents.

In one embodiment, the CDRs are those of 88D2C6 or its humanized counterparts, as exemplified in Tables 2B and 2D. In one embodiment, the CDRH1 comprises the amino acid sequence of SEQ ID NO: 22 or a variant thereof having one, two, or three deletions, additions, substitutions or the combinations thereof, the CDRH2 comprises the amino acid sequence of SEQ ID NO: 23 or a variant thereof having one, two, or three deletions, additions, substitutions or the combinations thereof, the CDRH3 comprises the amino acid sequence of SEQ ID NO: 24 or a variant thereof having one, two, or three deletions, additions, substitutions or the combinations thereof, the CDRL1 comprises the amino acid sequence of SEQ ID NO: 25 or 28 or a variant thereof having one, two, or three deletions, additions, substitutions or the combinations thereof, the CDRL2 comprises the amino acid sequence of SEQ ID NO: 26 or a variant thereof having one, two, or three deletions, additions, substitutions or the combinations thereof, and the CDRL3 comprises the amino acid sequence of SEQ ID NO: 27 or a variant thereof having one, two, or three deletions, additions, substitutions or the combinations thereof.

In one embodiment, the CDRH1 comprises the amino acid sequence of SEQ ID NO: 22 or a variant thereof having one, two, or three deletions, additions, substitutions or the combinations thereof, the CDRH2 comprises the amino acid sequence of SEQ ID NO: 23 or a variant thereof having one, two, or three deletions, additions, substitutions or the combinations thereof, the CDRH3 comprises the amino acid sequence of SEQ ID NO: 24 or a variant thereof having one, two, or three deletions, additions, substitutions or the combinations thereof, the CDRL1 comprises the amino acid sequence of SEQ ID NO: 25 or a variant thereof having one, two, or three deletions, additions, substitutions or the combinations thereof, the CDRL2 comprises the amino acid sequence of SEQ ID NO: 26 or a variant thereof having one, two, or three deletions, additions, substitutions or the combinations thereof, and the CDRL3 comprises the amino acid sequence of SEQ ID NO: 27 or a variant thereof having one, two, or three deletions, additions, substitutions or the combinations thereof.

In one embodiment, the CDRH1 comprises the amino acid sequence of SEQ ID NO: 22, the CDRH2 comprises the amino acid sequence of SEQ ID NO: 23, the CDRH3 comprises the amino acid sequence of SEQ ID NO: 24, the CDRL1 comprises the amino acid sequence of SEQ ID NO: 25 or 28, the CDRL2 comprises the amino acid sequence of SEQ ID NO: 26, and the CDRL3 comprises the amino acid sequence of SEQ ID NO: 27.

Also provided, in some embodiments, are those that include the same CDRs as 88D2C6 or its humanized counterparts. In some embodiments, the disclosed antibodies and fragments include those that bind to the same epitope as 88D2C6 or its humanized counterparts, and those that compete with any of them in binding to CCR8.

In some embodiments, the heavy chain variable region comprises an amino acid sequence selected from the group consisting of SEQ ID NO:3 (mouse or chimeric) and 29-31 (humanized), or a peptide having at least 90% sequence identity to an amino acid sequence selected from the group consisting of SEQ ID NO:3 (mouse or chimeric) and 29-31 (humanized).

In some embodiments, the light chain variable region comprises an amino acid sequence selected from the group consisting of SEQ ID NO:2 (mouse or chimeric), 32-34 and 41-43 (humanized), or a peptide having at least 90% sequence identity to an amino acid sequence selected from the group consisting of SEQ ID NO (mouse or chimeric): 2, 32-34 and 41-43 (humanized).

In some embodiments, the heavy chain variable region comprises the amino acid sequence of SEQ ID NO:29 and the light chain variable region comprises the amino acid sequence of any one of SEQ ID NO: 32-34 and 41-43. In some embodiments, the heavy chain variable region comprises the amino acid sequence of SEQ ID NO:30 and the light chain variable region comprises the amino acid sequence of any one of SEQ ID NO: 32-34 and 41-43. In some embodiments, the heavy chain variable region comprises the amino acid sequence of SEQ ID NO:31 and the light chain variable region comprises the amino acid sequence of any one of SEQ ID NO: 32-34 and 41-43. In some embodiments, the heavy chain variable region comprises the amino acid sequence of SEQ ID NO:29 and the light chain variable region comprises the amino acid sequence of SEQ ID NO:33.

In one embodiment, the CDRs are those of 137D1H10 or its humanized counterparts, as exemplified in Tables 3B and 3D. In one embodiment, the CDRH1 comprises the amino acid sequence of SEQ ID NO: 35 or a variant thereof having one, two, or three deletions, additions, substitutions or the combinations thereof, the CDRH2 comprises the amino acid sequence of SEQ ID NO: 36 or a variant thereof having one, two, or three deletions, additions, substitutions or the combinations thereof, the CDRH3 comprises the amino acid sequence of SEQ ID NO: 37 or a variant thereof having one, two, or three deletions, additions, substitutions or the combinations thereof, the CDRL1 comprises the amino acid sequence of SEQ ID NO: 25 or 28 or a variant thereof having one, two, or three deletions, additions, substitutions or the combinations thereof, the CDRL2 comprises the amino acid sequence of SEQ ID NO: 26 or a variant thereof having one, two, or three deletions, additions, substitutions or the combinations thereof, and the CDRL3 comprises the amino acid sequence of SEQ ID NO: 27 or a variant thereof having one, two, or three deletions, additions, substitutions or the combinations thereof.

In one embodiment, the CDRH1 comprises the amino acid sequence of SEQ ID NO: 35 or a variant thereof having one, two, or three deletions, additions, substitutions or the combinations thereof, the CDRH2 comprises the amino acid sequence of SEQ ID NO: 36 or a variant thereof having one, two, or three deletions, additions, substitutions or the combinations thereof, the CDRH3 comprises the amino acid sequence of SEQ ID NO: 37 or a variant thereof having one, two, or three deletions, additions, substitutions or the combinations thereof, the CDRL1 comprises the amino acid sequence of SEQ ID NO: 25 or a variant thereof having one, two, or three deletions, additions, substitutions or the combinations thereof, the CDRL2 comprises the amino acid sequence of SEQ ID NO: 26 or a variant thereof having one, two, or three deletions, additions, substitutions or the combinations thereof, and the CDRL3 comprises the amino acid sequence of SEQ ID NO: 27 or a variant thereof having one, two, or three deletions, additions, substitutions or the combinations thereof.

In one embodiment, the CDRH1 comprises the amino acid sequence of SEQ ID NO: 35, the CDRH2 comprises the amino acid sequence of SEQ ID NO: 36, the CDRH3 comprises the amino acid sequence of SEQ ID NO: 37, the CDRL1 comprises the amino acid sequence of SEQ ID NO: 25 or 28, the CDRL2 comprises the amino acid sequence of SEQ ID NO: 26, and the CDRL3 comprises the amino acid sequence of SEQ ID NO: 27.

Also provided, in some embodiments, are those that include the same CDRs as 137D1H10 or its humanized counterparts. In some embodiments, the disclosed antibodies and fragments include those that bind to the same epitope as 137D1H10 or its humanized counterparts, and those that compete with any of them in binding to CCR8.

In some embodiments, the heavy chain variable region comprises an amino acid sequence selected from the group consisting of SEQ ID NO:1 (mouse or chimeric) and 38-40 (humanized), or a peptide having at least 90% sequence identity to an amino acid sequence selected from the group consisting of SEQ ID NO:3 (mouse or chimeric) and 29-31 (humanized).

In some embodiments, the light chain variable region comprises an amino acid sequence selected from the group consisting of SEQ ID NO:2 (mouse or chimeric), 32-34 and 41-43 (humanized), or a peptide having at least 90% sequence identity to an amino acid sequence selected from the group consisting of SEQ ID NO (mouse or chimeric): 2, 32-34 and 41-43 (humanized).

In some embodiments, the heavy chain variable region comprises the amino acid sequence of SEQ ID NO:38 and the light chain variable region comprises the amino acid sequence of any one of SEQ ID NO: 32-34 and 41-43. In some embodiments, the heavy chain variable region comprises the amino acid sequence of SEQ ID NO:39 and the light chain variable region comprises the amino acid sequence of any one of SEQ ID NO: 32-34 and 41-43. In some embodiments, the heavy chain variable region comprises the amino acid sequence of SEQ ID NO:40 and the light chain variable region comprises the amino acid sequence of any one of SEQ ID NO: 32-34 and 41-43. In some embodiments, the heavy chain variable region comprises the amino acid sequence of SEQ ID NO:40 and the light chain variable region comprises the amino acid sequence of any one of SEQ ID NO:42.

The antibodies that contained these CDR regions, whether mouse, humanized or chimeric, had potent CCR8 binding and inhibitory activities. As shown in Example 4, certain residues within the CDR can be modified to retain or improve the property or reduce their potential to have post-translational modifications (PTMs). Such modified CDR can be referred to as affinity matured or de-risked CDRs (e.g., SEQ ID NO:25).

Modified CDRs can include those having one, two or three amino acid addition, deletion and/or substitutions. In some embodiments, the substitutions can be conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE A

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Bi-Functional Molecules and Combination Therapies

CCR8 is a chemokine and a tumor antigen. As a tumor antigen targeting molecule, an antibody or antigen-binding fragment specific to CCR8 can be combined with a second antigen-binding fragment specific to an immune cell, or an antigen-binding fragment specific to an immune checkpoint to generate a combination therapy or a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CCL1, CD3, CD16, CD19, CD28, and CD64. Other examples include PD-1, PD-L1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47.

As an immune checkpoint inhibitor, an antibody or antigen-binding fragment specific to CCR8 can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis.

Different format of bispecific antibodies are also provided. In some embodiments, each of the anti-PD-L1 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to CCR8, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Antibody-Drug Conjugates

In some embodiments, the antibodies or fragments may be conjugated to therapeutic agents, prodrugs, peptides, proteins, enzymes, viruses, lipids, biological response modifiers, pharmaceutical agents, or PEG.

In one embodiment, the antibodies or fragments of the disclosure are covalently attached to a drug moiety. The drug moiety may be, or be modified to include, a group reactive with a conjugation point on the antibody. For example, a drug moiety can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols.

In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 20, about 1 to about 10, about 2 to about 10, about 2 to about 9, about 1 to about 8, about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3.

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

The drug can be linked to the antibody or fragment by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the me linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio).

In some embodiments, the drug moiety is a cytotoxic or cytostatic agent, an immunosuppressive agent, a radioisotope, a toxin, or the like. The conjugate can be used for inhibiting the multiplication of a tumor cell or cancer cell, causing apoptosis in a tumor or cancer cell, or for treating cancer in a patient. The conjugate can be used accordingly in a variety of settings for the treatment of animal cancers. The conjugate can be used to deliver a drug to a tumor cell or cancer cell. Without being bound by theory, in some embodiments, the conjugate binds to or associates with a cancer cell expressing claudin 18.2, and the conjugate and/or drug can be taken up inside a tumor cell or cancer cell through receptor-mediated endocytosis.

Once inside the cell, one or more specific peptide sequences within the conjugate (e.g., in a linker) are hydrolytically cleaved by one or more tumor-cell or cancer-cell-associated proteases, resulting in release of the drug. The released drug is then free to migrate within the cell and induce cytotoxic or cytostatic or other activities. In some embodiments, the drug is cleaved from the antibody outside the tumor cell or cancer cell, and the drug subsequently penetrates the cell, or acts at the cell surface.

Examples of drug moieties or payloads are selected from the group consisting of DM1 (maytansine, N2'-deacetyl-N2'-(3-mercapto-1-oxopropyl)- or N2'-deacetyl-N2'-(3-mercapto-1-oxopropyl)-maytansine), me-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl] amino]propyl]-1-pyrrolidinyl]-1-[(1S)-1-methylpropyl]-4-oxobutyl]-N-methyl-(9C1)-L-valinamide), me-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-(αR, βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino] phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives. In some embodiments, the drug moiety is selected from the group consisting of me-MMAF and mc-Val-Cit-PABA-MMAE. In some embodiments, the drug moiety is a maytansinoid or an auristatin.

The antibodies or fragments may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, therromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. In some embodiments, the cancer cells in the patient express or overexpress CCR8. As provided above, CCR8 can be overexpressed in tumor cells, in particular gastric, pancreatic, esophageal, ovarian, and lung tumors. Inhibition of CCR8 has been shown to be useful for treating the tumors.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express CCR8.

Cellular therapies, such as chimeric antigen receptor (CAR) T-cell therapies, are also provided in the present disclosure. A suitable cell can be used, that is put in contact with an anti-CCR8 antibody of the present disclosure (or alternatively engineered to express an anti-CCR8 antibody of the present disclosure). In some embodiments, the antibody is presented in a chimeric antigen receptor (CAR). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4$^+$ T cell, a CD8$^+$ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is one or more of gastric, pancreatic, esophageal, ovarian, and lung cancers.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Diagnostic Methods

Over-expression of CCR8 is observed in certain tumor samples, and patients having CCR8-over-expressing cells are likely responsive to treatments with the anti-CCR8 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a CCR8 protein potentially present in the sample. Methods such as ELISA can be used, taking advantage of the anti-CCR8 antibody, to detect the presence of the CCR8 protein in the sample.

Presence of the CCR8 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Murine Monoclonal Antibodies Against Human CCR8

The human CCR8 protein was used to immunize different strains of mice, and hybridomas were generated accordingly. CCR8 positive binders were selected and subcloned. Subsequently, in vitro binding and functional screening were carried out and lead antibodies with highest binding affinity and strongest functional potency were identified.

The VH/VL sequences of the lead murine antibodies are provided in the table below.

TABLE 1

VH/VL sequence of the lead murine antibodies

| Name | Sequence (CDRs are underlined) | SEQ ID NO: |
|---|---|---|
| 137D1H10 VH | EVQLVESGGGLVQPKGSLKLSCTASGFTFNTYAMNWVRQAPGKGL EWVARIRSKANNYATYYADSVKDRFTISRDDSQRILYLQMNNLKA EDTAMYYCVRDRSRGEDYAMDYWGQGTSVTVSS | 1 |
| 137D1H10 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGAGTKLELK | 2 |
| 88D2C6 VH | EVQLVETGGGLVQPKGSLKLSCAASGFTFNPNAMNWVRQAPGKGL EWVARIRSKSNNYATYYADSVKDRFTISRDDSQSMLYLQMNNLKT EDTAMYYCVRGKDDGYRHYAMDYWGQGTSVTVSS | 3 |
| 88D2C6 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGAGTKLELK | 2 |
| 89B6F8 VH | DVKLVESGGGLVKPGGSLKLSCAASGFTFSSYTMSWVRQTPEKRL EWVATISSGDSYTYYPDSVKGRFTISRDNAKNTLYLRMSSLKSED TAMYYCTRDHYRYDVYAMDYWGQGTSVTVSS | 4 |
| 89B6F8 VL | DIVMTQSPSSLTVTAGEKVTMSCKSSQSLLNSGNQKNYLTWYQQK PGQPPKLLIYWASTRESGVPDRFTGSGSGTDFTLTISSVQAEDLA VYYCQNDYSYPLTFGAGTKLELK | 5 |
| 132H8E10 VH | QVQLKESGPGLVAPSQSLSITCTVSGFSLTGYAVNWVRQPTGKGL EWLGMIWGDGSTDYNSALKSRLSISKDNSKSQVFLKMNSLQTDDT ARYYCARDSLYGNYPAYWGQGTLVTVSA | 6 |
| 132H8E10 VL | DIQMTQSPSSLSASLGGKVTITCKASQDINKYMAWYQHKPGKGPR LLIHSTSTLQPGIPSRFSGSGSGRDYSFSISNLEPEDIATYYCLQ YDNLLTFGGGTKLEIK | 7 |
| 10F11B2 VH | QVQLKESGPGLVQPSQTLSLTCTVSGFSLTSYSVHWVRQHSGKTL VWMGRLWSDGDTSYNSAFTSRLSISRDTSKSQVFLKMNSLQTEDT GTYYCARKAPNGGAFDYWGQGVMVTVSS | 8 |
| 10F11B2 VL | QVVLTQPKSVSTSLESTVKLSCKLNSGNIGSYYVHWYQQHEGRSP TNMIYRDDKRPDGVPDRFSGSIDSSSNSAFLTINNVQTEDEAIYF CHSSDSSIKCIFGGGTKLTVL | 9 |
| 40H10F3 VH | QVQLKESGPGLVQPSQTLSLTCTVSGFSLTSYNVHWVRQPPGKGL EWMGRMRYYGDTSFSSALKSRLSISRDTSKNQVFLKMSSLQTDDT GTYYCTRGPPSYYRGDFFDYWGQGVMVAVSS | 10 |
| 40H10F3 VL | DIQMTQSPSLLSASVGDRVTINCKASLNINNYLNWYQQKLGEAPK | 11 |

TABLE 1-continued

VH/VL sequence of the lead murine antibodies

| Name | Sequence (CDRs are underlined) | SEQ ID NO: |
|---|---|---|
| VL | LLIDNTNNLQTGIPSRFSGSGSGTDYTLTISNLQPEDFGTYFCFQ HNGWPLTFGSGTKLEIK | |
| 53D6A9 VH | EVQLVESGGSLVQPGRSLKLSCAASGFTYNNYVMAWVRRAPTKGL EWVASISTDGVSTQYRDSVKGRFTISRDNAKTSLFLHMDSLRSED TATYYCAKDAARGLYGQGGYFDFWGQGVMVTVSS | 12 |
| 53D6A9 VL | DIQMTQSPASLSASLGETVSIECLASEGISNDLAWYQQKSGKSPQ LLIYAATRLEGGVPSRFSGSGSGTRFSLKISGMQFEDEADYFCQQ SYKYPWTFGGGTKLELK | 13 |
| 352H11C11 VH | EVQLVETGGGLVQPKGSLKLSCAASGFTFNTNAMNWVRQAPGKGL EWVARIRSKSNNYATYYADSVKDRFTISRDDSQSILYLQMNNLKT EDTAMYYCVRGGPIYHMDCWGQGTSVTVSS | 14 |
| 352H11C11 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGSGTKLEIK | 15 |
| 362G7D3 VH | EVQLVETGGGLVQPKGSLKLSCAASGFTFNTNAMNWVRQAPGKGL EWVARIRSKSNNYATYYADSVKDRFTISRDDSQSMLYLQMNNLKT EDTAMYYCVRDPGLRQGMDYWGQGTSVTVSS | 16 |
| 362G7D3 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGSGTKLEIK | 15 |
| 362H10A3 VH | EVQLVESGGGLVQPKGSLKLSCAASGFTFNTYAMNWVRQAPGKGL EWVARIRSKSNNYATYYADSVKDRFTISRDDSQSMLYLQMNNLKT EDTAMYYCVRGGGNYRGDYFDYWGQGTTLTVSS | 17 |
| 362H10A3 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGSGTKLEIK | 15 |
| 367D10E7 VH | EVQLVESGGGLVQPKGSLKLSCAASGFTFNTYAMNWVRQAPGKGL EWVARIRSKSNNYATYYADSVKDRFTISRDDSQSMLYLQMNNLKT EDTAMYYCVRYDRSYAMDYWGQGTSVTVSS | 18 |
| 367D10E7 VL v1 | QIVLTQSPAIMSASPGEKVTITCSASSSVSYMHWFQQKPGTSPKL WIYSTSNLASGVPARFSGSGSGTSYSLTISRMEAEDAATYYCQQR SSYPLTFGAGTKLELK | 19 |
| 367D10E7 VL v2 | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGAGTKLELK | 2 |
| 370D2C10 VH | EVQLIETGGGLVQPKGSLKLSCAASGFTFNTNAMNWVRQAPGKDL EWVSRIRTKSNNYATYYADSVKDRFTISRDDSQSMLYLQMNNLKT EDTAMYYCVTGTTVVAKEFAYWGQGTLVTVSA | 20 |
| 370D2C10 VL | DIVMTQAAPSVPVTPGESVSISCRSSKSLLHSNGNTYLYWFLQRP GQSPHLLIYRMSNLASGVPDRFSGSGSGTAFTLRISRVEAEDVGV YYCMQHLEYPFTFGSGTKLEIK | 21 |

Example 2. Binding to CCR8 on U2OS Cells

This example tested the antibodies' activity in binding to human CCR8 protein expressed on U2OS cells.

Chimeric antibodies (fused to human IgG1 constant regions) of a few of the above identified murine antibodies were expressed from cDNA. The antibodies were incubated with U2OS cells expressing the human CCR8. Among the antibodies tested, 88D2C6 and 137D1H10 exhibited considerably higher affinity than the rest, in a dose-dependent manner (FIG. 1).

Example 3. ADCC Measurement

Figure 2:
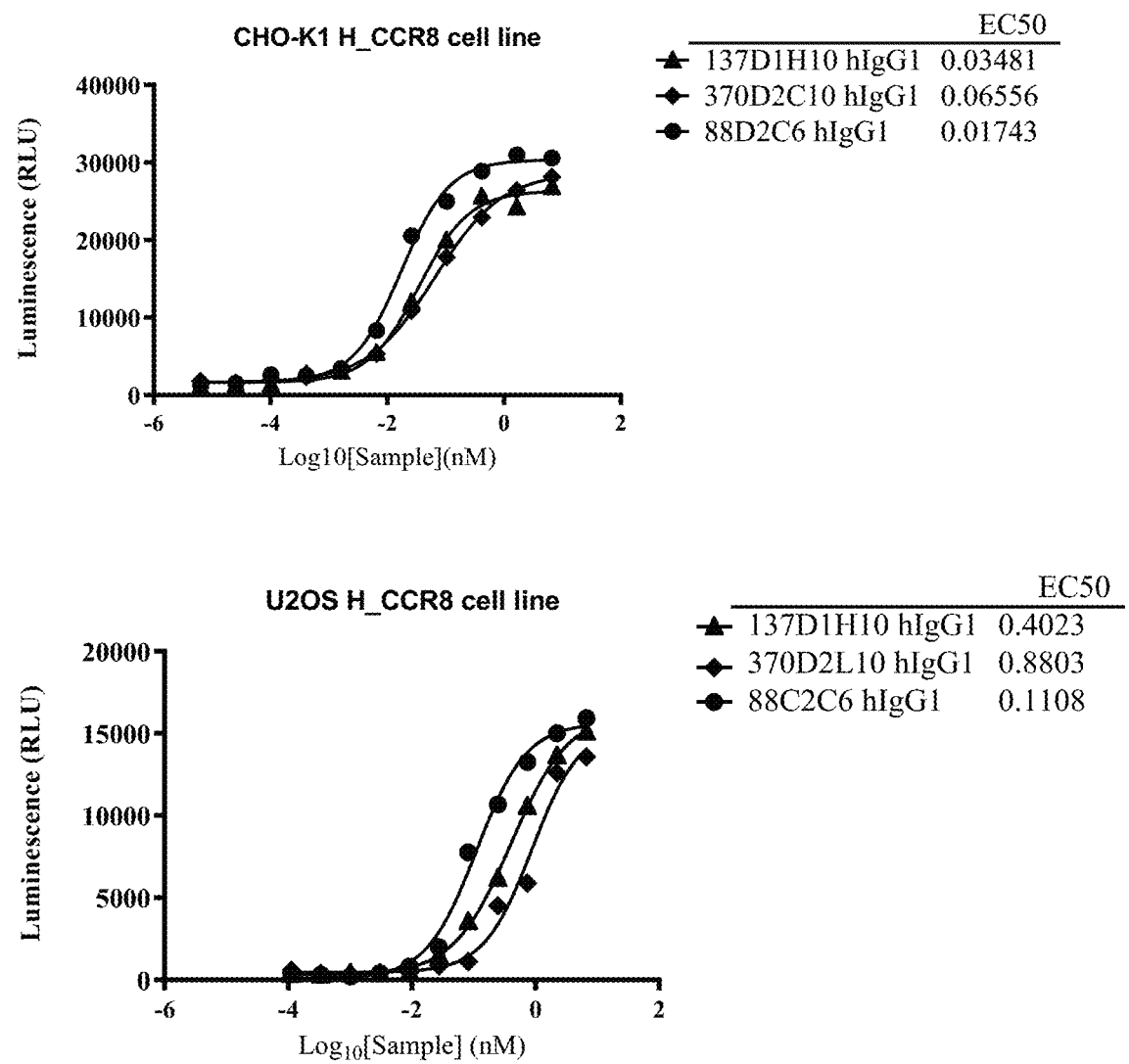
FIG. 2 shows the ADCC activity of three of the chimeric antibodies.

The potency of 88D2C6 and 137D1H10, along with 370D2C10 (all fused to human IgG1 constant regions, with ADCC-activating mutations in Fc), in mediating ADCC was measured with CCR8-overexpressing CHO K1 and U2OS cells. All three antibodies exhibited high ADCC activities (FIG. 2).

All three antibodies exhibited potent ADCC activities. Among them, however, 88D2C6 had considerably higher potency (EC50: 0.01743 nM with CHO cells and 0.1108 for U2OS cells).

Example 4. Humanization of the Mouse mAbs

The murine antibody variable region genes of 88D2C6 and 352H11C11 were employed to create humanized mAbs. The amino acid sequences of the VH and VL of mAb were compared against the available database of human Ig gene sequences to find the overall best-matching human germline Ig gene sequences. The CDRs of the murine antibodies were then grafted into the matched human sequences. The cDNA was synthesized and used to produce the humanized antibodies. Certain back mutations from the murine antibodies were then introduced back to the humanized antibodies. Certain amino acids were mutated to reduce the chance of post-translational modification.

The amino acid sequences of the humanized antibodies are provided below.

Humanized Sequences

A. 88D2C6

TABLE 2A

Humanization of 88D2C6-VH

| Name | Sequence | SEQ ID NO: |
|---|---|---|
| 88D2C6 VH | EVQLVETGGGLVQPKGSLKLSCAASGETFNPNAMNWVRQAPGKGL EWVARIRSKSNNYATYYADSVKDRFTISRDDSQSMLYLQMNNLKT EDTAMYYCVRGKDDGYRHYAMDYWGQGTSVTVSS | 3 |
| V1 (CDR grafting) | EVQLVESGGGLVQPGGSLKLSCAASGETFNPNAMNWVRQASGKGL EWVGRIRSKSNNYATYYADSVKDRFTISRDDSKNTAYLQMNSLKT EDTAVYYCTRGKDDGYRHYAMDYWGQGTTVTVSS | 29 |
| V2 (with back mutations) | EVQLVESGGGLVQPGGSLKLSCAASGETFNPNAMNWVRQASGKGL EWVGRIRSKSNNYATYYADSVKDRFTISRDDSKNTAYLQMNNLKT EDTAVYYCVRGKDDGYRHYAMDYWGQGTTVTVSS | 30 |
| V3 (with back mutations) | EVQLVESGGGLVQPGGSLKLSCAASGETFNPNAMNWVRQASGKGL EWVARIRSKSNNYATYYADSVKDRFTISRDDSKNTLYLQMNNLKT EDTAVYYCVRGKDDGYRHYAMDYWGQGTTVTVSS | 31 |

TABLE 2B

CDR Sequences

| CDR | Sequence | SEQ ID NO: |
|---|---|---|
| CDR-H1 | PNAMN | 22 |
| CDR-H2 | RIRSKSNNYATYYADSVKD | 23 |
| CDR-H3 | GKDDGYRHYAMDY | 24 |

TABLE 2C

Humanization of 88D2C6-VL

| Name | Sequence | SEQ ID NO: |
|---|---|---|
| 88D2C6 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGAGTKLELK | 2 |
| V1 (CDR grafting) | DIVMTQSPLSLPVTPGEPASISCRSSKSLLHSNANTYLYWYLQKP GQSPQLLIYRMSNLASGVPDRFSGSGSGTDFTLKISRVEAEDVGV YYCMQHLEYPFTFGGGTKVEIK | 32 |
| V2 (with back mutations) | DIVMTQSPLSLPVTPGEPASISCRSSKSLLHSNANTYLYWFLQKP GQSPQLLIYRMSNLASGVPDRFSGSGSGTAFTLKISRVEAEDVGV YYCMQHLEYPFTFGGGTKVEIK | 33 |
| V3 (with back mutations) | DIVMTQAPLSLPVTPGEPVSISCRSSKSLLHSNANTYLYWFLQKP GQSPQLLIYRMSNLASGVPDRFSGSGSGTAFTLKISRVEAEDVGV YYCMQHLEYPFTFGGGTKLEIK | 34 |

TABLE 2D

CDR Sequences

| CDR | Sequence | SEQ ID NO: |
|---|---|---|
| CDR-L1 | RSSKSLLHSNGNTYLY | 28 |
| CDR-L1 (PM site mutated) | RSSKSLLHSNANTYLY | 25 |
| CDR-L2 | RMSNLAS | 26 |
| CDR-L3 | MQHLEYPFT | 27 |

TABLE 2E

Humanized antibodies

|  | VL | VL v1 | VL v2 | VL v3 |
|---|---|---|---|---|
| VH | 88-xi | | | |
| VH v1 | | | 88-H1L2 | 88-H1L3 |
| VH v2 | | | 88-H2L2 | 88-H2L3 |
| VH v3 | | | 88-H3L2 | 88-H2L3 |

TABLE 3A

Humanization of 137D1H10-VH

| Name | Sequence | SEQ ID NO: |
|---|---|---|
| 137D1H10 VH | EVQLVESGGGLVQPKGSLKLSCTASGFTFNTYAMNWVRQAPGKGL EWVARIRSKANNYATYYADSVKDRFTISRDDSQRILYLQMNNLKA EDTAMYYCVRDRSRGEDYAMDYWGQGTSVTVSS | 1 |
| V1 (CDR grafting) | EVQLVESGGGLVQPGGSLKLSCAASGFTFNTYAMNWVRQASGKGL EWVGRIRSKANNYATYYADSVKDRFTISRDDSKNTAYLQMNSLKT EDTAVYYCTSDRSRGEDYAMDYWGQGTLVTVSS | 38 |
| V2 (with back mutations) | EVQLVESGGGLVQPGGSLKLSCAASGFTFNTYAMNWVRQASGKGL EWVGRIRSKANNYATYYADSVKDRFTISRDDSKNTAYLQMNNLKT EDTAVYYCVRDRSRGEDYAMDYWGQGTLVTVSS | 39 |
| V3 (with back mutations) | EVQLVESGGGLVQPGGSLKLSCAASGFTFNTYAMNWVRQASGKGL EWVARIRSKANNYATYYADSVKDRFTISRDDSKNTLYLQMNNLKT EDTAVYYCVRDRSRGEDYAMDYWGQGTLVTVSS | 40 |

TABLE 3B

CDR Sequences

| CDR | Sequence | SEQ ID NO: |
|---|---|---|
| CDR-H1 | TYAMN | 35 |
| CDR-H2 | RIRSKANNYATYYADSVKD | 36 |
| CDR-H3 | DRSRGEDYAMDY | 37 |

TABLE 3C

Humanization of 137D1H10-VL

| Name | Sequence | SEQ ID NO: |
|---|---|---|
| 137D1H10 VL | DIVMTQAAPSVPVTPGESVSISCRSSKSLLHSNGNTYLYWFLQRP GQSPQLLIYRMSNLASGVPDRFSGSGSGTAFTLRISRVEAEDVGV YYCMQHLEYPFTFGAGTKLELK | 2 |
| V1 (CDR grafting) | DIVMTQSPLSLPVTPGEPASISCRSSKSLLHSNANTYLYWYLQKP GQSPQLLIYRMSNLASGVPDRFSGSGSGTDFTLKISRVEAEDVGV YYCMQHLEYPFTFGQGTKLEIK | 41 |

TABLE 3C-continued

Humanization of 137D1H10-VL

| Name | Sequence | SEQ ID NO: |
|---|---|---|
| V2 (with back mutations) | DIVMTQSPLSLPVTPGEPASISCRSSKSLLHSNANTYLYWFLQKP GQSPQLLIYRMSNLASGVPDRFSGSGSGTAFTLKISRVEAEDVGV YYCMQHLEYPFTFGQGTKLEIK | 42 |
| V3 (with back mutations) | DIVMTQSPLSLPVTPGEPVSISCRSSKSLLHSNANTYLYWFLQKP GQSPQLLIYRMSNLASGVPDRFSGSGSGTAFTLKISRVEAEDVGV YYCMQHLEYPFTFGQGTKLEIK | 43 |

TABLE 3D

CDR Sequences

| CDR | Sequence | SEQ ID NO: |
|---|---|---|
| CDR-L1 | RSSKSLLHSNGNTYLY | 28 |
| CDR-L1 (PM site mutated) | RSSKSLLHSNANTYLY | 25 |
| CDR-L2 | RMSNLAS | 26 |
| CDR-L3 | MQHLEYPFT | 27 |

TABLE 3E

Humanized antibodies

|  | VL | VL v1 | VL v2 | VL v3 |
|---|---|---|---|---|
| VH | 137-xi | | | |
| VH v1 | | | | |
| VH v2 | | | 137-H2L2 | 137-H2L3 |
| VH v3 | | | 137-H3L2 | 137-H3L3 |

Example 5. Testing of Humanized Antibodies

This example tested some of the humanized antibodies for their binding affinity to CCR8 and their ability to induce ADCC.

Figure 3:
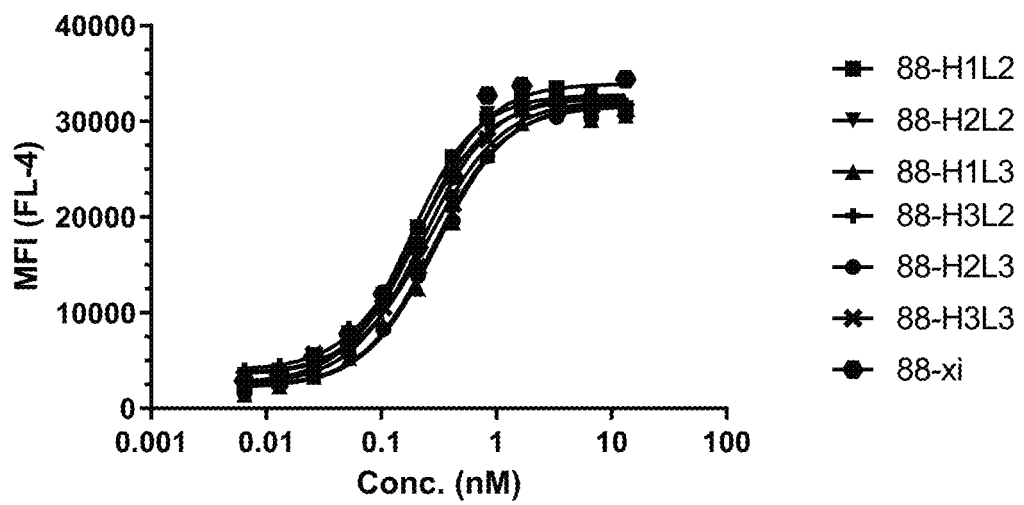
FIG. 3 shows that humanized 88D2C6 antibodies have high affinities.
Figure 3:
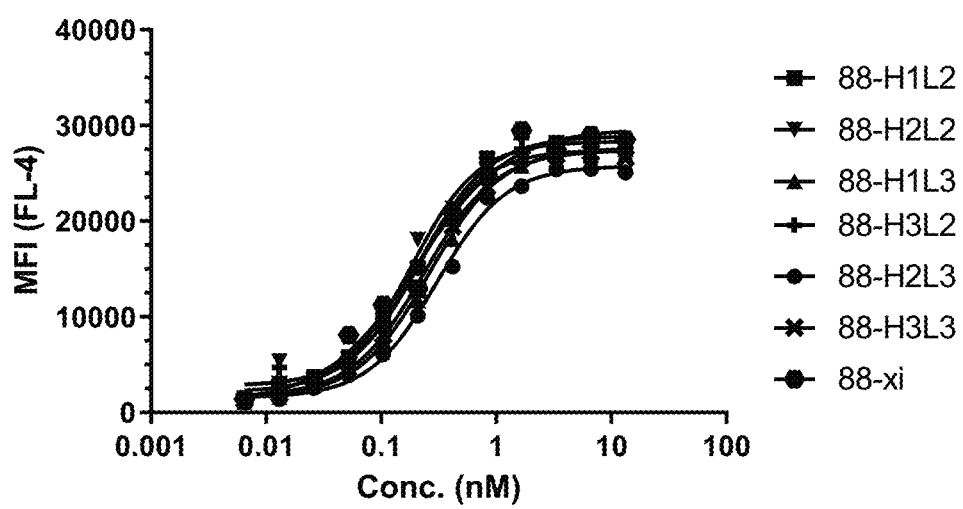

The experimental procedures are similar to Examples 2-3. FIG. 3 shows the affinities of humanized antibodies of 88D2C6. Apparently, all of them had high affinity (see also Table 4).

TABLE 4A

Binding to CCR8 expressed in CHO-K1 cells

| | 88-H1L2 | 88-H1L3 | 88-H2L2 | 88-H2L3 | 88-H3L2 | 88-H3L3 | 88-xi |
|---|---|---|---|---|---|---|---|
| Bottom | 2669 | 2143 | 2494 | 2276 | 3937 | 3474 | 3631 |
| Top | 32782 | 31947 | 32830 | 31610 | 32495 | 32214 | 33947 |
| LogEC50 | −0.7515 | −0.5189 | −0.6391 | −0.5461 | −0.6861 | −0.5826 | −0.6548 |
| HillSlope | 1.502 | 1.377 | 1.404 | 1.408 | 1.382 | 1.345 | 1.480 |
| EC50 | 0.1772 | 0.3028 | 0.2296 | 0.2844 | 0.2060 | 0.2615 | 0.2214 |
| Span | 30113 | 29804 | 30336 | 29334 | 28557 | 28740 | 30316 |

TABLE 4B

Binding to CCR8 expressed in U2OS cells

| | 88-H1L2 | 88-H1L3 | 88-H2L2 | 88-H2L3 | 88-H3L2 | 88-H3L3 | 88-xi |
|---|---|---|---|---|---|---|---|
| Bottom | 2106 | 1542 | 2756 | 1530 | 2826 | 1623 | 1027 |
| Top | 28891 | 27635 | 28329 | 25780 | 27435 | 27421 | 29659 |
| LogEC50 | −0.6779 | −0.5797 | −0.7241 | −0.5119 | −0.6841 | −0.6289 | −0.6921 |
| HillSlope | 1.409 | 1.387 | 1.524 | 1.450 | 1.521 | 1.378 | 1.097 |
| EC50 | 0.2099 | 0.2632 | 0.1888 | 0.3077 | 0.2070 | 0.2350 | 0.2032 |
| Span | 26785 | 26092 | 25574 | 24250 | 24609 | 25798 | 28632 |

Figure 4:
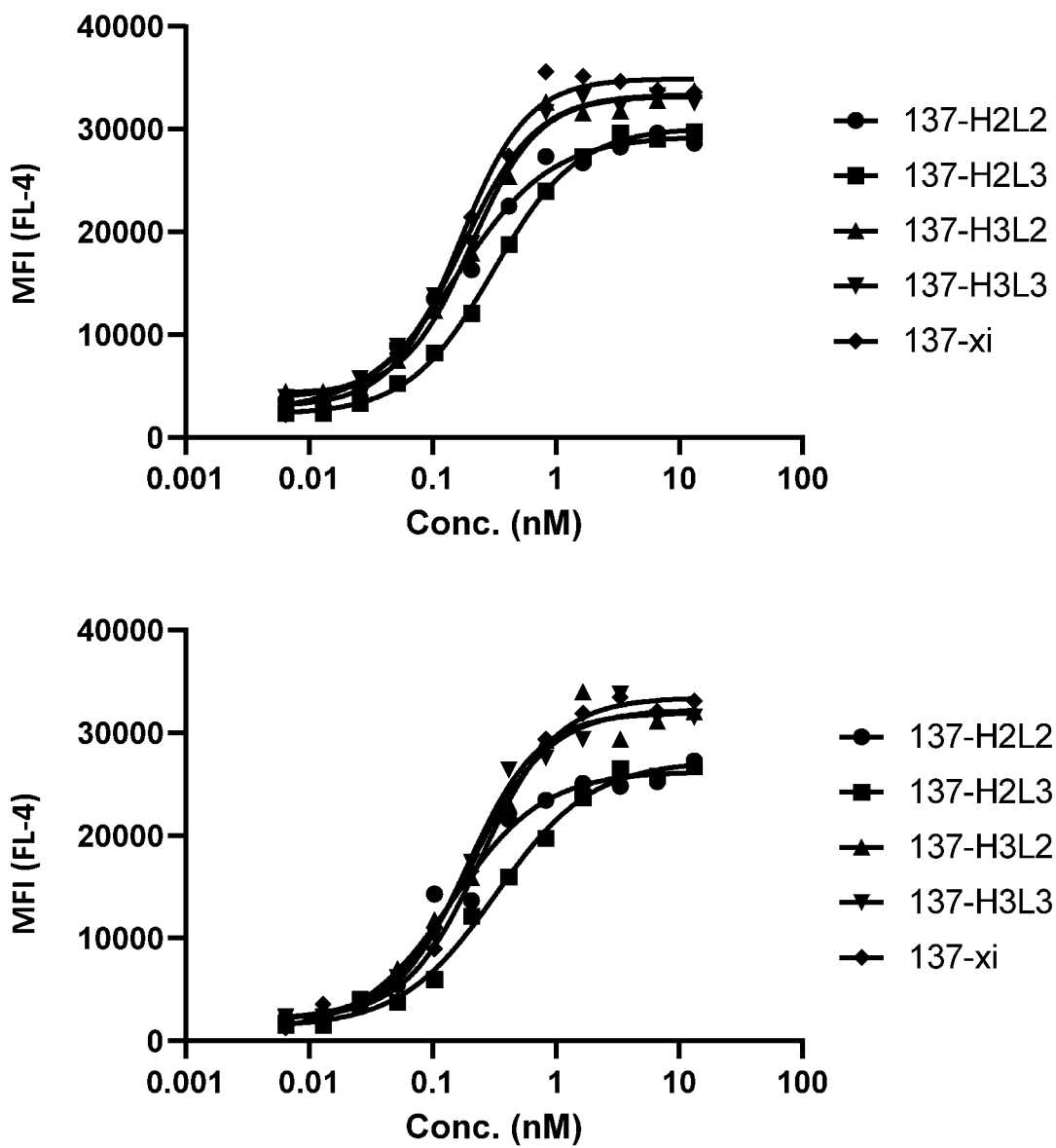
FIG. 4 shows that humanized 137D1H10 antibodies have high affinities.

FIG. 4 shows the affinities of humanized antibodies of 137D1H10 (data in Table 5).

TABLE 5A

Binding to CCR8 expressed in CHO-K1 cells

|  | 137-H2L2 | 137-H2L3 | 137-H3L2 | 137-H3L3 | 137-xi |
|---|---|---|---|---|---|
| Bottom | 2548 | 2244 | 4264 | 3820 | 3032 |
| Top | 29347 | 30182 | 33198 | 33389 | 34947 |
| LogEC50 | −0.7893 | −0.5055 | −0.6843 | −0.7538 | −0.7792 |
| HillSlope | 1.141 | 1.272 | 1.592 | 1.449 | 1.581 |
| EC50 | 0.1625 | 0.3123 | 0.2069 | 0.1763 | 0.1663 |
| Span | 26799 | 27937 | 28934 | 29569 | 31915 |

TABLE 5B

Binding to CCR8 expressed in U2OS cells

|  | 137-H2L2 | 137-H2L3 | 137-H3L2 | 137-H3L3 | 137-xi |
|---|---|---|---|---|---|
| Bottom | 915.4 | 1322 | 2065 | 2098 | 2172 |
| Top | 26251 | 27254 | 32257 | 31927 | 33430 |
| LogEC50 | −0.8422 | −0.4841 | −0.6897 | −0.7169 | −0.6052 |
| HillSlope | 1.171 | 1.122 | 1.351 | 1.492 | 1.422 |
| EC50 | 0.1438 | 0.3280 | 0.2043 | 0.1919 | 0.2482 |
| Span | 25336 | 25932 | 30192 | 29829 | 31258 |

Figure 5:
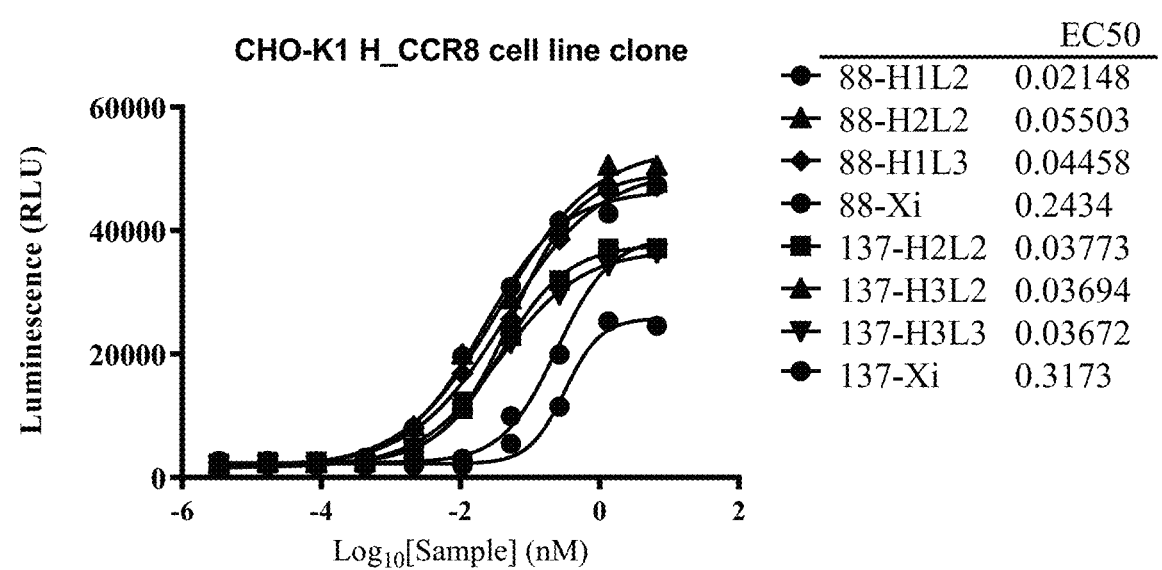
FIG. 5 shows that, compared to the chimeric antibodies, the humanized antibodies have significantly higher ADCC activities.

In terms of ADCC (FIG. 5), surprisingly, all humanized antibodies exhibited greatly higher (about 5 to 10-fold) ADCC inducing activity than the chimeric counterparts.

Example 6. Cell-Based Antibody Binding

This example compared 137-H3L2 (LM-108) with reference antibodies with respect to cell-based binding Cell based binding of LM-108 and reference Ab (synthesized according to WO2020138489) to human CCR8 overexpressing cells (HEK293/H_CCR8) were assessed using flow cytometry. The human CCR8 overexpressing HEK293 (HEK293/H_CCR8) and parental HEK293 cells were incubated with titrated LM-108, reference Ab and its isotype control (from 200 nM, 4 folds dilutions, 12 points) at 4° C. for 60 minutes. The cells were washed with FACS buffer twice, then stained with fluorescent conjugated secondary antibody (Alexa Fluor® 647 Goat Anti-Human IgG, Jackson, 109-605-098) at 4° C. for 60 minutes. After the cells were washed twice and they were analyzed by flow cytometry.

Figure 6:
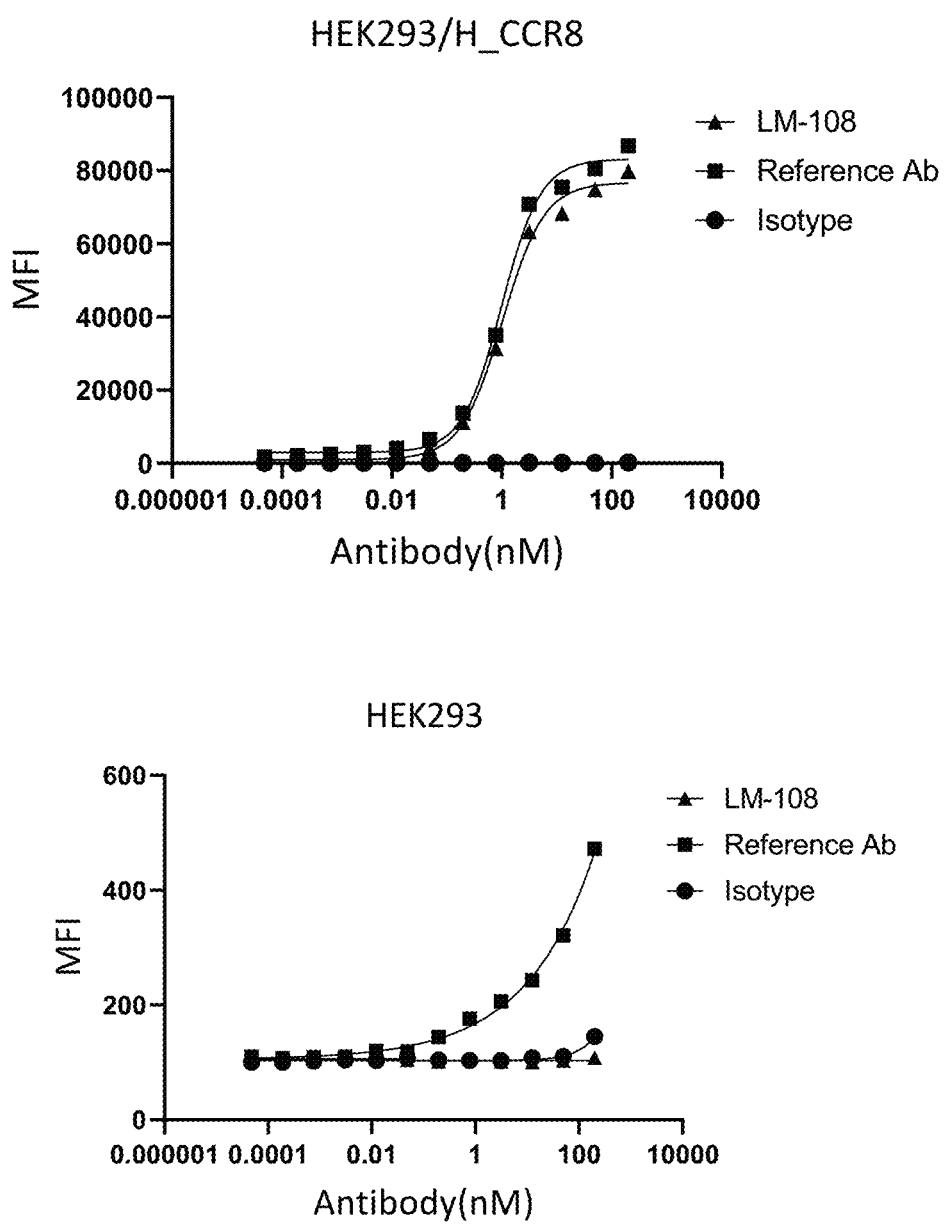
FIG. 6 shows the results of cell-based binding of LM-108 and reference antibody to human CCR8 by flow cytometry. Upper panel: FACS binding of LM-108 on human CCR8 expressing HEK293. Lower panel: FACS binding of LM-108 on HEK293 cells.

Both LM-108 and the reference Ab effectively bound to HEK293/H_CCR8 cells in a dose dependent manner, at $EC_{50}$ of 1.03 nM and 0.99 nM, respectively (FIG. 6a and Table 6A). There was no non-specific binding observed for LM-108 but reference Ab showed slight nonspecific binding on parental HEK293 cells (FIG. 6b and Table 6B).

TABLE 6A

Binding to CCR8-expressing HEK293 cells

| Antibody | EC50 (nM) | Max (MFI) |
|---|---|---|
| LM-108 | 1.028 | 76795 |
| Reference Ab | 0.9938 | 86817 |
| Isotype | N.A. | 192 |

TABLE 6B

Binding to Non-CCR8-expressing HEK293 cells

| Antibody | EC50 (nM) | Max (MFI) |
|---|---|---|
| LM-108 | N.A. | 108 |
| Reference Ab | N.A. | 472 |
| Isotype | N.A. | 145 |

Figure 7:
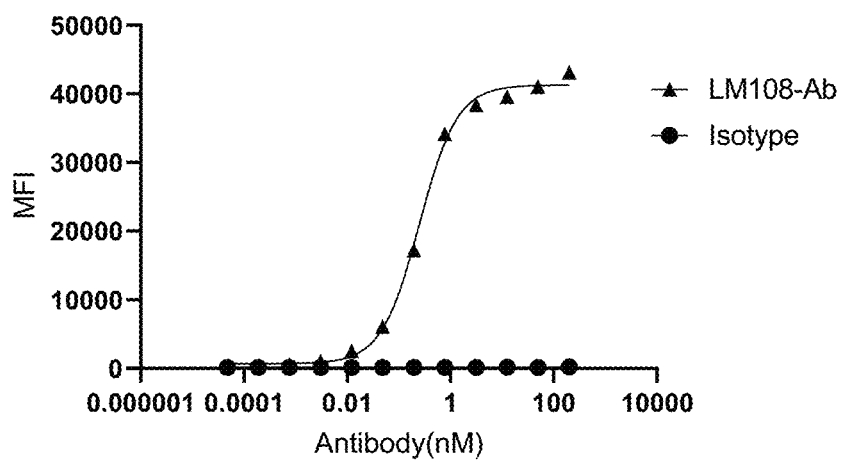
FIG. 7 shows cell-based binding of LM-108 to human CCR8 high expressing U2OS cells by flow cytometry.

Cell-based binding of LM-108 on cells with high levels of CCR8 expression was assessed using flow cytometry. The cells used were U2OS (U2OS/H_CCR8). As shown in FIG. 7 and Table 7, LM-108 could effectively bind to U2OS/H_CCR8 cells in a dose dependent manner with an $EC_{50}$ of 0.25 nM.

TABLE 7

Binding to High-CCR8-expressing U2OS cells

| Antibody | EC50 (nM) | Max (MFI) |
|---|---|---|
| LM-108 | 0.2503 | 43087 |
| Isotype | N.A. | 215 |

Figure 8:
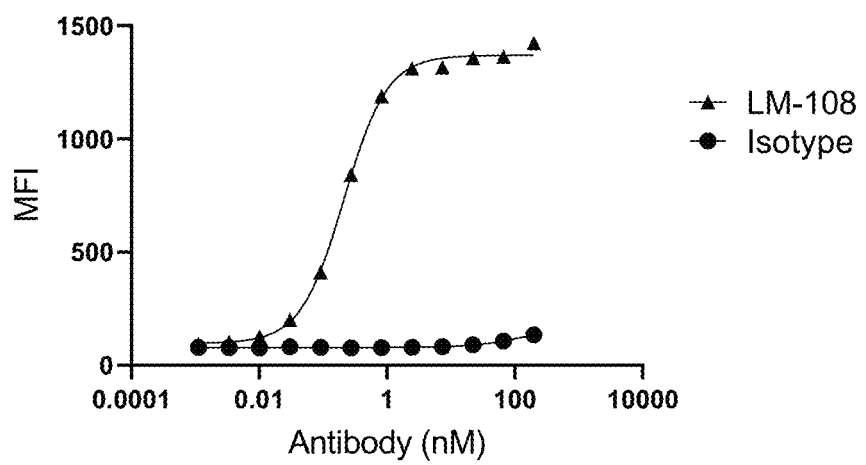
FIG. 8 shows cell-based binding of LM-108 to human CCR8 low expressing Jurkat cells by flow cytometry.

Cell-based binding of LM-108 on cells with low levels of CCR8 expression was also assessed using flow cytometry. The cells used were Jurkat engineering cells (Jurkat/H_CCR8). As shown in FIG. 8 and Table 8, LM-108 could effectively bind to Jurkat/H_CCR8 cells in a dose dependent manner with an EC50 of 0.21 nM.

TABLE 8

Binding to Low-CCR8-expressing Jurkat cells

| Antibody | EC50 (nM) | Max (MFI) |
|---|---|---|
| LM-108 | 0.2124 | 1423 |
| Isotype | N.A. | 134 |

Example 7. ADCC Report Gene Assay

This example shows the results of an ADCC reporter gene assay targeting different CCR8-expressing cells.

ADCC Reporter Gene Assay Targeting U2OS/H_CCR8

The ADCC activity of LM-108 was assessed with a reporter gene assay with CD16a (158v) expressing Jurkat/NFAT-luc reporter cells as effector cells. Human CCR8 overexpressing U2OS cells were used as target cells. U2OS/H_CCR8 cells were planted at the density of 1E4 cells per well in 96-well plate overnight, then co-cultured with $1.5 \times 10^5$ effecter cells each well and the titrated LM-108 and the isotype control to final concentration from 10 μg/ml, 5 times dilution, and 10 points. After incubation under 37° C. for 6 hours, One-Glo (Promega) was added for luminescence detection.

Figure 9:
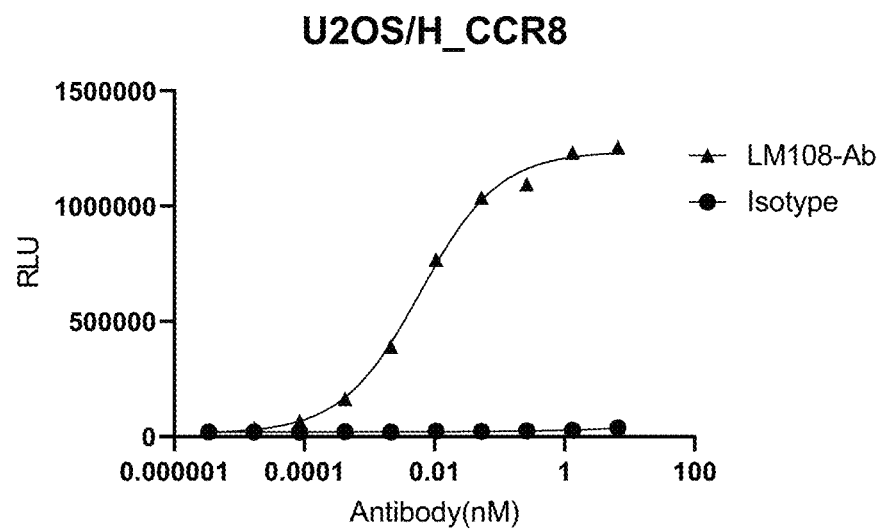
FIG. 9 shows the results of ADCC Reporter Gene Assay of LM-108 with Jurkat/CD16a(158v)/NFAT-luc cells, targeting CCR8 high expressing U2OS cells.

The results are shown in FIG. 9. LM-108 exhibited potent ADCC effect ($EC_{50}$=0.00605 nM) with Jurkat/CD16a/NFAT-luc reporter cells targeting U2OS/H_CCR8 cells.

ADCC Reporter Gene Assay Targeting Jurkat/H_CCR8

ADCC activity of LM-108 as assessed by reporter gene assay with CD16a (158v) expressing Jurkat/NFAT-luc reporter cells as effector cells. Human CCR8 low expressing Jurkat cells were generated as target cells to mimic the expression level on tumor associated Tregs.

Figure 10:
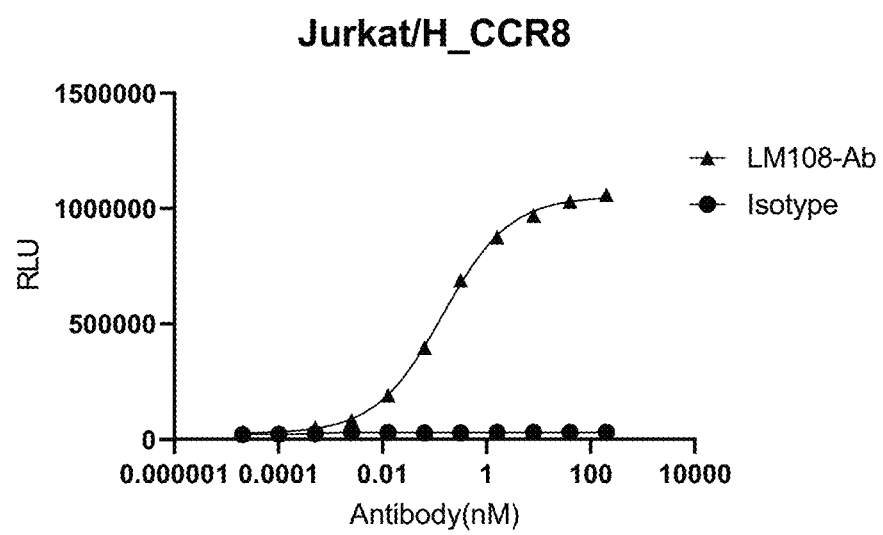
FIG. 10 shows the results of ADCC Reporter Gene Assay of LM-108 with Jurkat/CD16a(158v)/NFAT cells, targeting CCR8 low expressing Jurkat cells.

Effector cells (Jurkat reporter cell) and target cells (Jurkat/H_CCR8) at ratio of 3:1 were mixed with the titrated LM-108 and the isotype control (final concentration from 200 nM, 5 times dilution, 11 points). After incubation under 37° C. for 6 hours, One-Glo (Promega) was added for luminescence detection. As shown in FIG. 10, LM-108 had dose-dependent ADCC effect with an $EC_{50}$=0.14 nM.

ADCC Effect of LM-108 Towards Human CCR8 Over-Expressing HEK293 (HEK293/H_CCR8) and HEK293 Cells with Primary Human PBMCs Effector cells (hPBMCs) and target cells (HEK293/H_CCR8 or HEK293) at a ratio of 50:1 were mixed with the titrated LM-108 and the isotype control (final concentration from 10 nM, 7 folds dilution, 12 points). After incubation under 37° C. for 6 hours, 50 μl supernatant from each well was analyzed by Cytotoxicity Detection Kit (Roche, 04744934001)

Figure 11:
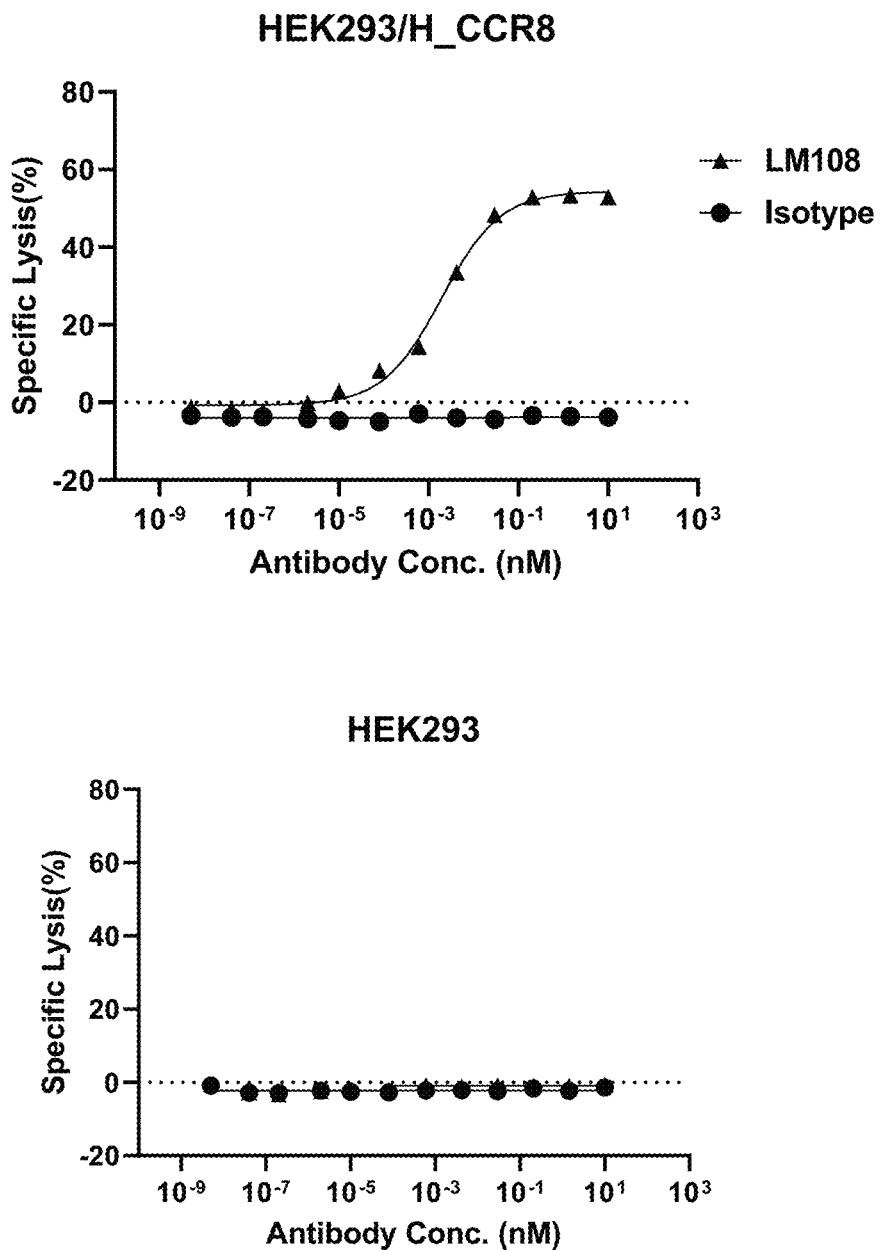
FIG. 11 shows the results of ADCC testing of LM-108 with hPBMCs targeting CCR8-expressing cells (upper panel) or control cells (lower panel).

As shown in FIG. 11A, LM-108 exhibited specific and strong ADCC effect towards CCR8-expressing HEK293 cells in a dose-dependent manner with an $EC_{50}$ of 0.002 nM (FIG. 6a). No nonspecific killing observed on parental HEK293 cells (FIG. 11B).

Example 8. Testing of Antibody-Dependent Cellular Phagocytosis (ADCP)

In this example, the antibody-dependent cellular phagocytosis (ADCP) effect of LM-108 towards human CCR8-overexpressed CHO-K1 cells was evaluated with monocyte-derived macrophages (MDMs) by FACS.

The effector cells, MDMs, were induced from monocytes isolated from human PBMC with the presence of 100 ng/mL of human M-CSF for 7 days. The target cells were CHO-K1 (negative control) and CHO-K1 cells overexpressing human CCR8 which labeled CFSE. The effector cells, CFSE-labeled target cells, and titrated test antibody LM-108 or its isotype control were incubated in a 37° C., 5% CO2 incubator for 2 hours. Cells were washed with FACS buffer (1×DPBS+2% FBS), then stained with APC-conjugated human CD14 antibody to identify the macrophages. After wash twice with FACS buffer, the samples were analyzed by flow cytometry. Phagocytosis index was determined as the percentage of CD14-APC+/CFSE+ double positive cells in total $CD14^+$ positive cells.

Figure 12:
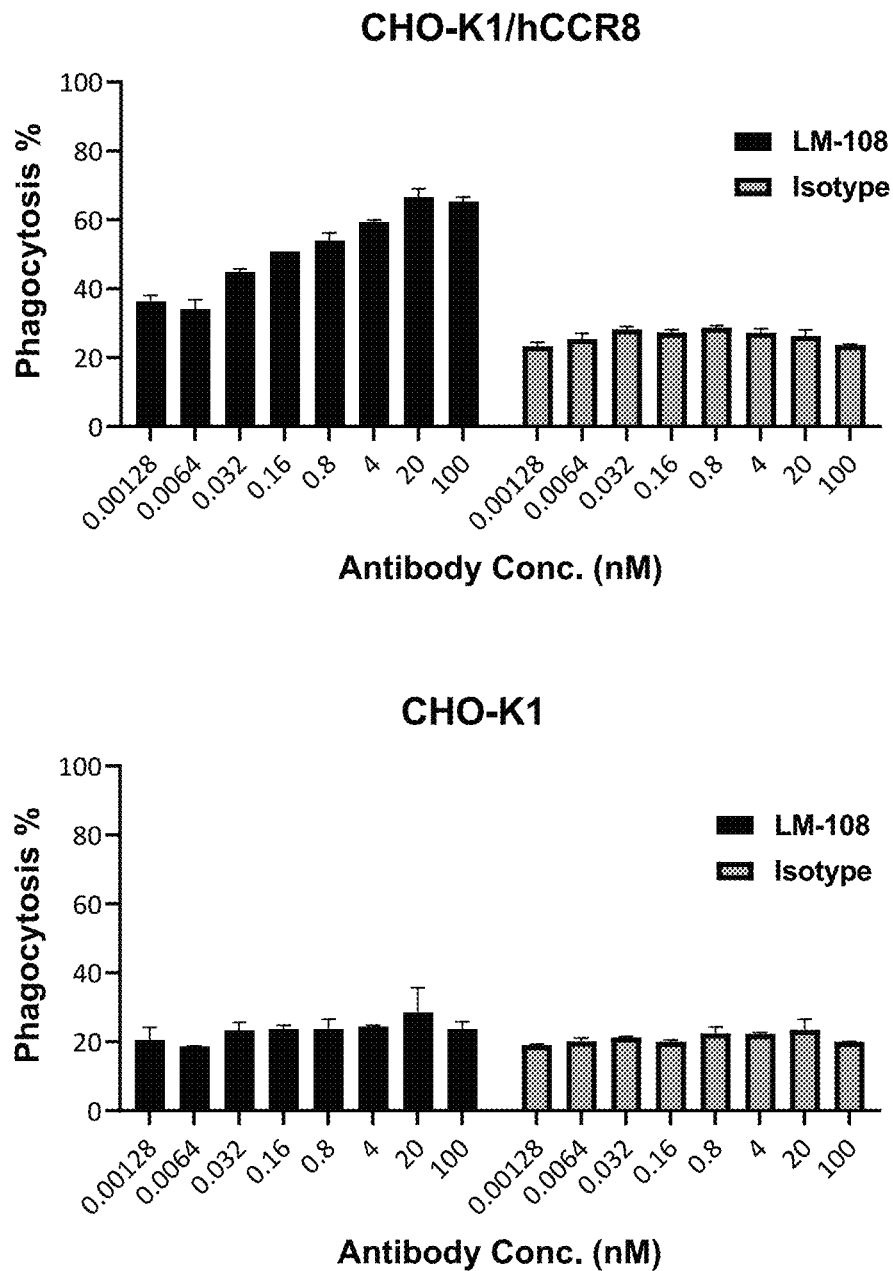
FIG. 12 shows ADCP of LM-108 with Monocyte-derived Macrophage by FACS. Upper panel: ADCP of LM-108 LM-108 towards human CCR8 over expressing CHO-K1 cells. Lower panel: ADCP of LM-108 LM-108 towards control CHO-K1 cells.

As shown in FIG. 12A-B, LM-108 had specific and dose dependent phagocytosis toward human CCR8 overexpressing CHO-K1 cells, but not control cells.

ADCP of LM-108 with Monocyte-derived Macrophage (MDM) was also measured by Operetta. The effector cells, MDMs, were induced from monocytes isolated from human PBMC with the presence of 100 ng/mL of human M-CSF for 6 days. Then the effector cells were seeded into a black 96-well plate with clear bottom at $2 \times 10^4$ count/well and cultured for another 2 days for adherence. The target cells were Jurkat (negative control) and human CCR8 over expressing Jurkat cells (Jurka/H_CCR8). The CFSE-labeled target cells and test antibody LM-108 or its isotype control were added into the plate with macrophages, and incubated in a 37° C., 5% CO2 incubator for 2 hours. The effector cell:target cell ratio is 1:2. Cells were washed and stained with APC-conjugated human CD14 antibody to identify the macrophages. After washed twice, cells were fixed using 4% paraformaldehyde (PFA) dilution and stored in a 4° C. freezer at dark before taking photos by Operetta.

Figure 13:
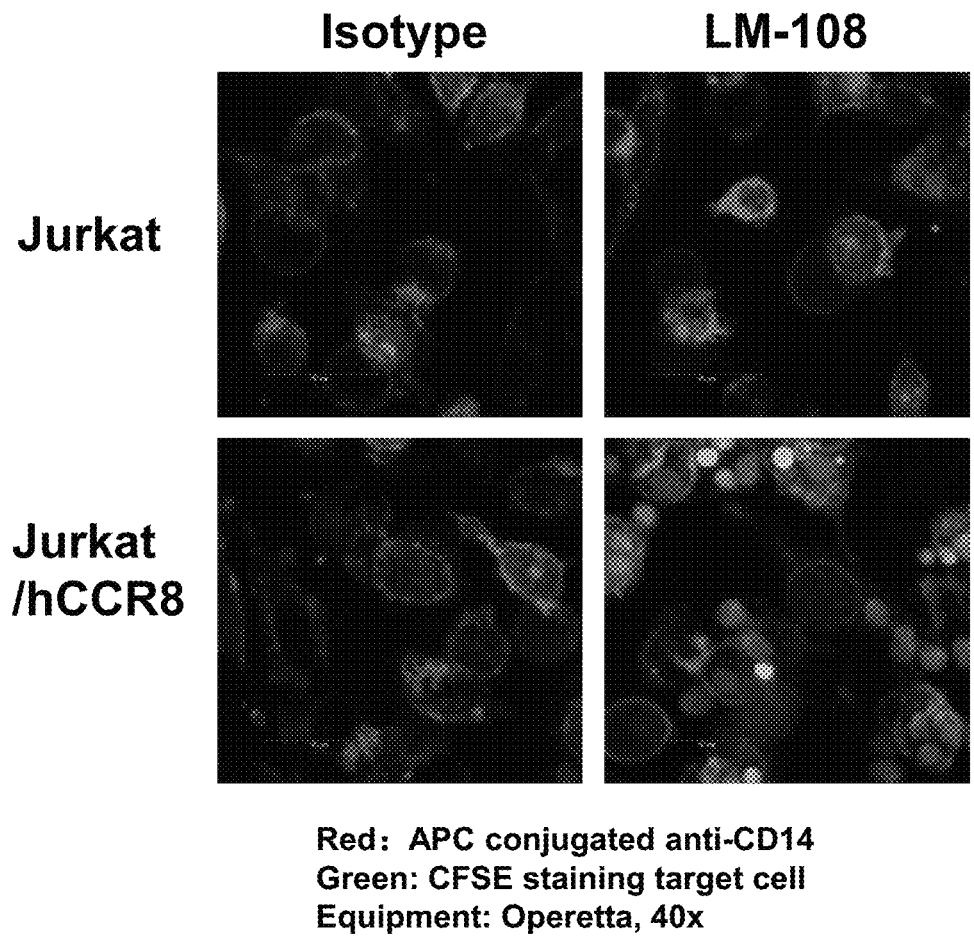
FIG. 13 presents imaging results of ADCP of LM-108 with Monocyte-derived Macrophage by Operetta.

As shown in FIG. 13, LM-108 induced ADCP towards human CCR8-overexpressed Jurkat cells, while its isotype control did not. Neither LM-108 nor the isotype control induced obvious phagocytosis towards Jurkat cells.

Example 9. In Vivo Efficacy

In this example, in vivo efficacy studies of LM-108 or its mouse surrogate were performed.

The first experiment was performed on a CT26 syngeneic model with LM-108m, a surrogate antibody for LM-108. In this study, each mouse was inoculated subcutaneously at the right axillary (lateral) with CT26 tumor cell ($5 \times 10^5$) in 0.1 ml of PBS for tumor development. The animals were randomly grouped into 4 groups (n=7) on the third day after cell inoculation, then treatment started. PBS group as vehicle, LM-108m and mPD-1 antibody at dose of 10 mg/kg was administrated via introperitoneal (i.p.) as single agent or combo at day 0, day 3, day 7, day 10, day 14 and day 17. The experiment was terminated at day 18 due to the average tumor volume of control group reached more than 2000 $mm^3$.

Tumor sizes were measured three times weekly in two dimensions using a caliper and the volume was expressed in $mm^3$ using the formula: $V=0.5a \times b^2$ where a and b were the long and short diameters of the tumor, respectively. The tumor sizes were then used for the calculations of T/C (%) values. T/C (%) was calculated using the formula: $T/C \% = (T_i-T_0)/(V_i-V_0) \times 100$, $T_i$ was the average tumor volume of a treatment group on a given day, $T_0$ was the average tumor volume of the treatment group on the first day of treatment, $V_i$ was the average tumor volume of the vehicle control group on the same day with $T_i$, and $V_0$ was the average tumor volume of the vehicle group on the first day of treatment. TGI was calculated for each group using the formula: TGI (%)=[100−T/C].

Figure 14:
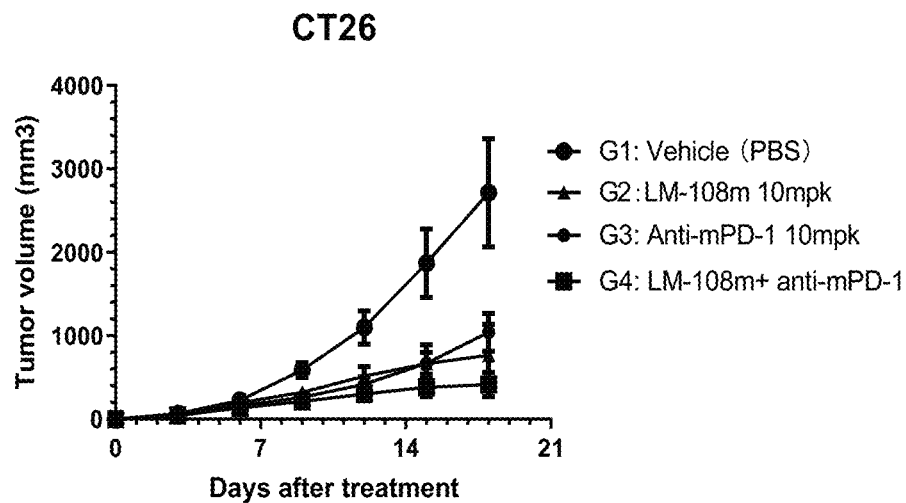
FIG. 14 shows tumor growth curves of CT26 tumor-bearing mice post administration of LM-108m and anti-mPD-1 Ab, in an in vivo efficacy study of LM-108m on CT26 syngeneic model with BALB/c mice.

FIG. 14 shows the tumor growth curve of CT26 tumor-bearing Balb/c mice post administration of LM-108m and anti-mPD-1 Ab. LM-108m as single agent or in combination of mPD-1 antibody showed strong anti-tumor activity (Table 9). Data points represent group (n=7) mean, error bars represent standard error of the mean (SEM). p value was calculated based on tumor size by t-test, compared with vehicle control using PBS.

TABLE 9

| | In vivo Efficacy (CT26 syngeneic model) | | | | | | |
|---|---|---|---|---|---|---|---|
| | 0 | 3 | 6 | 9 | 12 | 15 | 18 |
| | Days after treatment T/C (%) | | | | | | |
| G2: LM-108 m 10 mpk | — | 72.161 | 86.504 | 54.453 | 47.024 | 35.639 | 28.219 |
| G3: Anti-mPD-1 Ab 10 mpk | — | 59.926 | 70.322 | 44.463 | 38.057 | 35.773 | 38.326 |
| G4: LM-108 m + mPD-1 Ab | — | 70.506 | 60.774 | 35.973 | 27.413 | 20.386 | 15.292 |
| | Days after treatment TGI (%) | | | | | | |
| G2: LM-108 m 10 mpk | — | 27.839 | 13.496 | 45.547 | 52.976 | 64.361 | 71.781 |
| G3: Anti-mPD-1 Ab 10 mpk | — | 40.074 | 29.678 | 55.537 | 61.943 | 64.227 | 61.674 |
| G4: LM-108 m + mPD-1 Ab | — | 29.494 | 39.226 | 64.027 | 72.587 | 79.614 | 84.708 |
| | Days after treatment P value | | | | | | |
| G2: LM-108 m 10 mpk | — | 0.053 | 0.385 | 0.024 | 0.026 | 0.025 | 0.023 |
| G3: Anti-mPD-1 Ab 10 mpk | — | 0.024 | 0.073 | 0.007 | 0.008 | 0.026 | 0.044 |
| G4: LM-108 m + mPD-1 Ab | — | 0.037 | 0.017 | 0.002 | 0.006 | 0.01 | 0.012 |

The second experiment used human CCR8 ki mice which were purchased from BIOCYTOGEN. Each hCCR8 ki mouse was inoculated subcutaneously at the right axillary (lateral) with MC38 tumor cell ($1\times10^6$) in 0.1 ml of PBS for tumor development. The animals were randomly grouped on the third day after cell inoculation, then treatment started for the efficacy study. LM-108 at dose of 10 mg/kg was administrated via introperitoneal (i.p.) at day 0, day 3, day 7, day 10. The experiment was terminated when average tumor volume of control group reached more than 2000 mm$^3$.

Tumor sizes were measured three times weekly in two dimensions using a caliper and the volume was expressed in mm$^3$ using the formula: $V=0.5a\times b^2$ where a and b were the long and short diameters of the tumor, respectively. The tumor sizes were then used for the calculations of T/C (%) values. T/C (%) was calculated using the formula: T/C %=$(T_i-T_0)/(V_i-V_0)\times 100$, $T_i$ was the average tumor volume of a treatment group on a given day, $T_0$ was the average tumor volume of the treatment group on the first day of treatment, $V_i$ was the average tumor volume of the vehicle control group on the same day with $T_i$, and $V_0$ was the average tumor volume of the vehicle group on the first day of treatment. TGI was calculated for each group using the formula: TGI (%)=[100−T/C]. Data points represent group (n=8) mean, error bars represent standard error of the mean (SEM). p value was calculated based on tumor size by t-test, compared with Vehicle Control.

Figure 15:
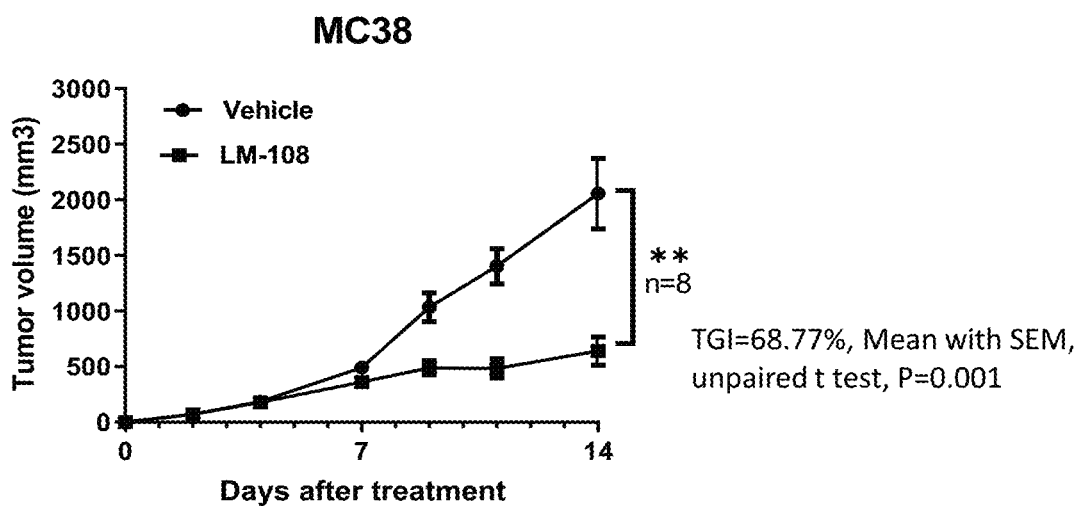
FIG. 15 shows tumor growth curves of MC38 tumor-bearing mice post administration of LM-108m and vehicle, in an in vivo efficacy study of LM-108 on MC38 syngeneic model with hCCR8 ki mice.

FIG. 15 shows the tumor growth curve of MC38 tumor-bearing mice post administration of LM-108, and the data are summarized in Table 10. LM-108 showed potent tumor inhibitory effects.

TABLE 10

| | In vivo Efficacy (MC38 syngeneic model) | | | | | | |
|---|---|---|---|---|---|---|---|
| | Days after treatment | | | | | | |
| P Value | 0 | 2 | 4 | 7 | 9 | 11 | 14 |
| LM-108 vs. Vehicle | — | 0.985 | 0.503 | 0.042 | 0.002 | 0 | 0.001 |
| T/C (%) | 0 | 3 | 5 | 7 | 10 | 12 | 14 |
| LM-108 vs. Vehicle | — | 99.68 | 95.326 | 73.673 | 47.349 | 34.464 | 31.23 |
| TGI (%) | 0 | 3 | 5 | 7 | 10 | 12 | 14 |
| LM-108 vs. Vehicle | — | 0.32 | 4.674 | 26.327 | 52.651 | 65.536 | 68.77 |

Example 10. Cytotoxicity Assessment

This example evaluated the cytotoxicity of an antibody-drug conjugate, LM-108-vc-MMAE (Monomethyl auristatin E), on human CCR8 expressing HEK293 cells.

To evaluate if LM-108 can be used for ADC development, cytotoxicity of MMAE conjugated LM-108 was assessed by co-culture the human CCR8 expressing HEK293 cells and the titrated ADC of LM-108-vc-MMAE.

HEK293/H_CCR8 cells were planted at the density of $1.5 \times 10^4$ cells per well in 96-well plate overnight, then co-cultured with titrated LM-108-vc-MMAE to final concentration from 100 nm, 3 times dilution, 9 points. After incubation under 37° C. for 96 hours, Cell-Titer-Glo (Promega) was added for cell viability evaluation.

Figure 16:
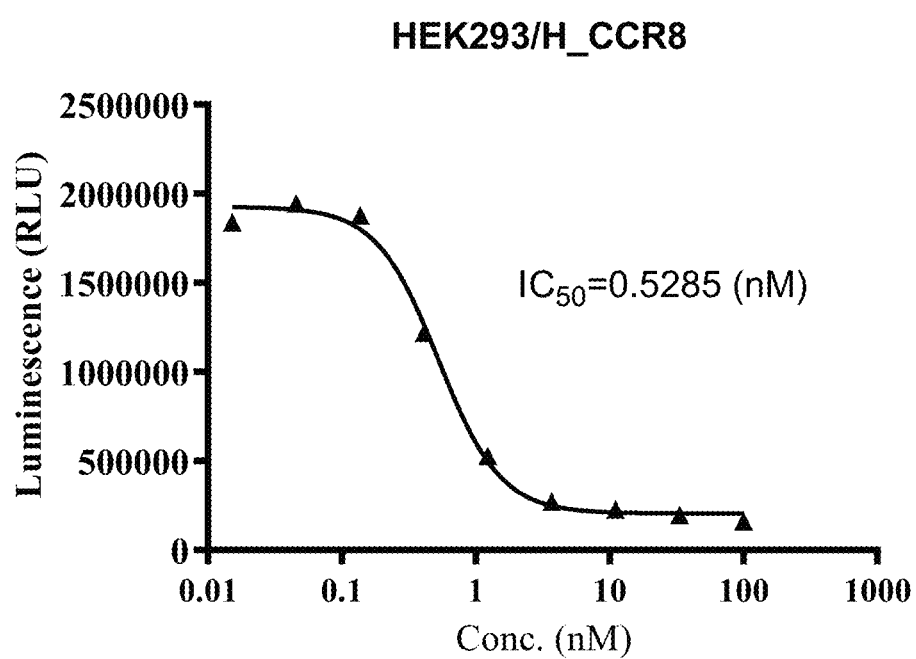
FIG. 16 shows the results of cytotoxicity evaluation of LM-108-vc-MMAE on hCCR8 expressing cells.

As shown in FIG. 16, MMAE conjugated LM-108 had potent cytotoxicity (IC50=0.5285 nM) on human CCR8-expressing HEK293 cells.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A monoclonal antibody or antigen-binding fragment thereof having binding specificity to a human chemokine (C—C motif) receptor 8 (CCR8) protein, wherein the antibody or fragment thereof each comprises a heavy chain variable region comprising heavy chain complementarity determining regions CDRH1, CDRH2, and CDRH3 and a light chain variable region comprising complementarity determining regions CDRL1, CDRL2, and CDRL3, and wherein:

the CDRH1 comprises the amino acid sequence of SEQ ID NO: 35,
the CDRH2 comprises the amino acid sequence of SEQ ID NO: 36, the CDRH3 comprises the amino acid sequence of SEQ ID NO: 37,
the CDRL1 comprises the amino acid sequence of SEQ ID NO: 25,
the CDRL2 comprises the amino acid sequence of SEQ ID NO: 26, and
the CDRL3 comprises the amino acid sequence of SEQ ID NO: 27.

2. The antibody or antigen-binding fragment thereof of claim 1, wherein the heavy chain variable region comprises an amino acid sequence selected from the group consisting of SEQ ID NO: 38-40, and the light chain variable region comprises an amino acid sequence selected from the group consisting of SEQ ID NO: 32-34 and 41-43.

3. The antibody or antigen-binding fragment thereof of claim 1, wherein the heavy chain variable region comprises the amino acid sequence of SEQ ID NO:40, and the light chain variable region comprises the amino acid sequence of SEQ ID NO:42.

4. The antibody or antigen-binding fragment thereof of claim 1, which is humanized.

5. The antibody or antigen-binding fragment of claim 1, which is capable of mediating antibody-dependent cellular cytotoxicity (ADCC).

6. The antibody or antigen-binding fragment of claim 5, which is fucosylated.

7. A composition comprising the antibody or antigen-binding fragment thereof of claim 1 and a pharmaceutically acceptable carrier.

8. The composition of claim 7, further comprising a second antibody having specificity to a tumor antigen.

9. The antibody or antigen-binding fragment thereof of claim 1, wherein the antigen-binding fragment is F(ab')$_2$, Fab', Fab, Fv, or scFv.

* * * * *

SEQUENCE LISTING

```
<160> NUMBER OF SEQ ID NOS: 44

<210> SEQ ID NO 1
<211> LENGTH: 123
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Glu Ser Gly Gly Gly Leu Val Gln Pro Lys Gly
1               5                   10                  15

Ser Leu Lys Leu Ser Cys Thr Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ala Asn Asn Tyr Ala Thr Tyr Tyr Ala Asp
    50                  55                  60

Ser Val Lys Asp Arg Phe Thr Ile Ser Arg Asp Asp Ser Gln Arg Ile
65                  70                  75                  80

Leu Tyr Leu Gln Met Asn Asn Leu Lys Ala Glu Asp Thr Ala Met Tyr
                85                  90                  95

Tyr Cys Val Arg Asp Arg Ser Arg Gly Glu Asp Tyr Ala Met Asp Tyr
            100                 105                 110

Trp Gly Gln Gly Thr Ser Val Thr Val Ser Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Synthetic

<400> SEQUENCE: 2

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
```

```
                    50                  55                  60
Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                     85                  90                  95

Leu Glu Tyr Pro Phe Thr Phe Gly Ala Gly Thr Lys Leu Glu Leu Lys
                    100                 105                 110
```

<210> SEQ ID NO 3
<211> LENGTH: 124
<212> TYPE: PRT
<213> ORGANISM: Artificial Sequence
<220> FEATURE:
<223> OTHER INFORMATION: Synthetic

<400> SEQUENCE: 3

```
Glu Val Gln Leu Val Glu Thr Gly Gly Gly Leu Val Gln Pro Lys Gly
  1               5                  10                  15

Ser Leu Lys Leu Ser Cys Ala Ala Ser Gly Phe Thr Phe Asn Pro Asn
                 20                  25                  30

Ala Met Asn Trp Val Arg Gln Ala Pro Gly Lys Gly Leu Glu Trp Val
             35                  40                  45

Ala Arg Ile Arg Ser Lys Ser Asn Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Arg Gly Lys Asp Gly Tyr Arg His Tyr Ala Met Asp
             100                 105                 110

Tyr Trp Gly Gln Gly Thr Ser Val Thr Val Ser Ser
                115                 120
```

<210> SEQ ID NO 4
<211> LENGTH: 121
<212> TYPE: PRT
<213> ORGANISM: Artificial Sequence
<220> FEATURE:
<223> OTHER INFORMATION: Synthetic

<400> SEQUENCE: 4

```
Asp Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Tyr
                 20                  25                  30

Thr Met Ser Trp Val Arg Gln Thr Pro Glu Lys Arg Leu Glu Trp Val
             35                  40                  45

Ala Thr Ile Ser Ser Gly Asp Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Arg Met Ser Ser Leu Lys Ser Glu Asp Thr Ala Met Tyr Tyr Cys
                 85                  90                  95

Thr Arg Asp His Tyr Arg Tyr Asp Val Tyr Ala Met Asp Tyr Trp Gly
             100                 105                 110

Gln Gly Thr Ser Val Thr Val Ser Ser
            115                 120
```

<210> SEQ ID NO 5
<211> LENGTH: 113
<212> TYPE: PRT
<213> ORGANISM: Artificial Sequence
<220> FEATURE:
<223> OTHER INFORMATION: Synthetic

<400> SEQUENCE: 5

```
Asp Ile Val Met Thr Gln Ser Pro Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys
```

<210> SEQ ID NO 6
<211> LENGTH: 118
<212> TYPE: PRT
<213> ORGANISM: Artificial Sequence
<220> FEATURE:
<223> OTHER INFORMATION: Synthetic

<400> SEQUENCE: 6

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Ala Val Asn Trp Val Arg Gln Pro Thr Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Ser Leu Tyr Gly Asn Tyr Pro Ala Tyr Trp Gly Gln Gly Thr
            100                 105                 110

Leu Val Thr Val Ser Ala
        115
```

<210> SEQ ID NO 7
<211> LENGTH: 106
<212> TYPE: PRT
<213> ORGANISM: Artificial Sequence
<220> FEATURE:
<223> OTHER INFORMATION: Synthetic

<400> SEQUENCE: 7

```
Asp Ile Gln Met Thr Gln Ser Pro Ser Ser Leu Ser Ala Ser Leu Gly
1               5                   10                  15
```

Gly Lys Val Thr Ile Thr Cys Lys Ala Ser Gln Asp Ile Asn Lys Tyr
            20                  25                  30

Met Ala Trp Tyr Gln His Lys Pro Gly Lys Gly Pro Arg Leu Leu Ile
        35                  40                  45

His Ser Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Thr
                85                  90                  95

Phe Gly Gly Gly Thr Lys Leu Glu Ile Lys
            100                 105

<210> SEQ ID NO 8
<211> LENGTH: 118
<212> TYPE: PRT
<213> ORGANISM: Artificial Sequence
<220> FEATURE:
<223> OTHER INFORMATION: Synthetic

<400> SEQUENCE: 8

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Ser Val His Trp Val Arg Gln His Ser Gly Lys Thr Leu Val Trp Met
        35                  40                  45

Gly Arg Leu Trp Ser Asp Gly Asp Thr Ser Tyr Asn Ser Ala Phe Thr
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Gly Thr Tyr Tyr Cys Ala
                85                  90                  95

Arg Lys Ala Pro Asn Gly Gly Ala Phe Asp Tyr Trp Gly Gln Gly Val
            100                 105                 110

Met Val Thr Val Ser Ser
        115

<210> SEQ ID NO 9
<211> LENGTH: 111
<212> TYPE: PRT
<213> ORGANISM: Artificial Sequence
<220> FEATURE:
<223> OTHER INFORMATION: Synthetic

<400> SEQUENCE: 9

Gln Val Val Leu Thr Gln Pro Lys Ser Val Ser Thr Ser Leu Glu Ser
1               5                   10                  15

Thr Val Lys Leu Ser Cys Lys Leu Asn Ser Gly Asn Ile Gly Ser Tyr
            20                  25                  30

Tyr Val His Trp Tyr Gln Gln His Glu Gly Arg Ser Pro Thr Asn Met
        35                  40                  45

Ile Tyr Arg Asp Asp Lys Arg Pro Asp Gly Val Pro Asp Arg Phe Ser
    50                  55                  60

Gly Ser Ile Asp Ser Ser Asn Ser Ala Phe Leu Thr Ile Asn Asn
65                  70                  75                  80

Val Gln Thr Glu Asp Glu Ala Ile Tyr Phe Cys His Ser Ser Asp Ser

```
                        85                  90                  95

Ser Ile Lys Cys Ile Phe Gly Gly Gly Thr Lys Leu Thr Val Leu
                100                 105                 110

<210> SEQ ID NO 10
<211> LENGTH: 121
<212> TYPE: PRT
<213> ORGANISM: Artificial Sequence
<220> FEATURE:
<223> OTHER INFORMATION: Synthetic

<400> SEQUENCE: 10

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Asn Val His Trp Val Arg Gln Pro Pro Gly Lys Gly Leu Glu Trp Met
        35                  40                  45

Gly Arg Met Arg Tyr Tyr Gly Asp Thr Ser Phe Ser Ser Ala Leu Lys
    50                  55                  60

Ser Arg Leu Ser Ile Ser Arg Asp Thr Ser Lys Asn Gln Val Phe Leu
65                  70                  75                  80

Lys Met Ser Ser Leu Gln Thr Asp Asp Thr Gly Thr Tyr Tyr Cys Thr
                85                  90                  95

Arg Gly Pro Pro Ser Tyr Tyr Arg Gly Asp Phe Phe Asp Tyr Trp Gly
            100                 105                 110

Gln Gly Val Met Val Ala Val Ser Ser
        115                 120

<210> SEQ ID NO 11
<211> LENGTH: 107
<212> TYPE: PRT
<213> ORGANISM: Artificial Sequence
<220> FEATURE:
<223> OTHER INFORMATION: Synthetic

<400> SEQUENCE: 11

Asp Ile Gln Met Thr Gln Ser Pro Ser Leu Leu Ser Ala Ser Val Gly
1               5                   10                  15

Asp Arg Val Thr Ile Asn Cys Lys Ala Ser Leu Asn Ile Asn Asn Tyr
            20                  25                  30

Leu Asn Trp Tyr Gln Gln Lys Leu Gly Glu Ala Pro Lys Leu Leu Ile
        35                  40                  45

Asp Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Asn Leu Gln Pro
65                  70                  75                  80

Glu Asp Phe Gly Thr Tyr Phe Cys Phe Gln His Asn Gly Trp Pro Leu
                85                  90                  95

Thr Phe Gly Ser Gly Thr Lys Leu Glu Ile Lys
            100                 105

<210> SEQ ID NO 12
<211> LENGTH: 124
<212> TYPE: PRT
<213> ORGANISM: Artificial Sequence
<220> FEATURE:
<223> OTHER INFORMATION: Synthetic

<400> SEQUENCE: 12
```

Glu Val Gln Leu Val Glu Ser Gly Gly Ser Leu Val Gln Pro Gly Arg
1               5                   10                  15

Ser Leu Lys Leu Ser Cys Ala Ala Ser Gly Phe Thr Tyr Asn Asn Tyr
            20                  25                  30

Val Met Ala Trp Val Arg Arg Ala Pro Thr Lys Gly Leu Glu Trp Val
        35                  40                  45

Ala Ser Ile Ser Thr Asp Gly Val Ser Thr Gln Tyr Arg Asp Ser Val
    50                  55                  60

Lys Gly Arg Phe Thr Ile Ser Arg Asp Asn Ala Lys Thr Ser Leu Phe
65                  70                  75                  80

Leu His Met Asp Ser Leu Arg Ser Glu Asp Thr Ala Thr Tyr Tyr Cys
                85                  90                  95

Ala Lys Asp Ala Ala Arg Gly Leu Tyr Gly Gln Gly Gly Tyr Phe Asp
            100                 105                 110

Phe Trp Gly Gln Gly Val Met Val Thr Val Ser Ser
        115                 120

<210> SEQ ID NO 13
<211> LENGTH: 107
<212> TYPE: PRT
<213> ORGANISM: Artificial Sequence
<220> FEATURE:
<223> OTHER INFORMATION: Synthetic

<400> SEQUENCE: 13

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Ala Thr Arg Leu Glu Gly Gly Val Pro Ser Arg Phe Ser Gly
    50                  55                  60

Ser Gly Ser Gly Thr Arg Phe Ser Leu Lys Ile Ser Gly Met Gln Phe
65                  70                  75                  80

Glu Asp Glu Ala Asp Tyr Phe Cys Gln Gln Ser Tyr Lys Tyr Pro Trp
                85                  90                  95

Thr Phe Gly Gly Gly Thr Lys Leu Glu Leu Lys
            100                 105

<210> SEQ ID NO 14
<211> LENGTH: 120
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Ile

```
            65                  70                  75                  80
Leu Tyr Leu Gln Met Asn Asn Leu Lys Thr Glu Asp Thr Ala Met Tyr
                85                  90                  95

Tyr Cys Val Arg Gly Gly Pro Ile Tyr His Met Asp Cys Trp Gly Gln
            100                 105                 110

Gly Thr Ser Val Thr Val Ser Ser
        115                 120

<210> SEQ ID NO 15
<211> LENGTH: 112
<212> TYPE: PRT
<213> ORGANISM: Artificial Sequence
<220> FEATURE:
<223> OTHER INFORMATION: Synthetic

<400> SEQUENCE: 15

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 16
<211> LENGTH: 121
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Pro Gly Leu Arg Gln Gly Met Asp Tyr Trp Gly
            100                 105                 110

Gln Gly Thr Ser Val Thr Val Ser Ser
        115                 120

<210> SEQ ID NO 17
<211> LENGTH: 123
```

-continued

<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Gly Asn Tyr Arg Gly Asp Tyr Phe Asp Tyr
            100                 105                 110

Trp Gly Gln Gly Thr Thr Leu Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Tyr Asp Arg Ser Tyr Ala Met Asp Tyr Trp Gly Gln
            100                 105                 110

Gly Thr Ser Val Thr Val Ser Ser
        115                 120

<210> SEQ ID NO 19
<211> LENGTH: 106
<212> TYPE: PRT
<213> ORGANISM: Artificial Sequence
<220> FEATURE:
<223> OTHER INFORMATION: Synthetic

<400> SEQUENCE: 19

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met

```
                    20                  25                  30
His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 20
<211> LENGTH: 122
<212> TYPE: PRT
<213> ORGANISM: Artificial Sequence
<220> FEATURE:
<223> OTHER INFORMATION: Synthetic

<400> SEQUENCE: 20

Glu Val Gln Leu Ile Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Asp Leu Glu Trp Val
        35                  40                  45

Ser Arg Ile Arg Thr Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Thr Gly Thr Thr Val Val Ala Lys Glu Phe Ala Tyr Trp
            100                 105                 110

Gly Gln Gly Thr Leu Val Thr Val Ser Ala
        115                 120

<210> SEQ ID NO 21
<211> LENGTH: 112
<212> TYPE: PRT
<213> ORGANISM: Artificial Sequence
<220> FEATURE:
<223> OTHER INFORMATION: Synthetic

<400> SEQUENCE: 21

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro His Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95
```

```
Leu Glu Tyr Pro Phe Thr Phe Gly Ser Gly Thr Lys Leu Glu Ile Lys
            100                 105                 110
```

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

```
Pro Asn Ala Met Asn
1               5
```

<210> SEQ ID NO 23
<211> LENGTH: 19
<212> TYPE: PRT
<213> ORGANISM: Artificial Sequence
<220> FEATURE:
<223> OTHER INFORMATION: Synthetic

<400> SEQUENCE: 23

```
Arg Ile Arg Ser Lys Ser Asn Asn Tyr Ala Thr Tyr Tyr Ala Asp Ser
1               5                   10                  15

Val Lys Asp
```

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

```
Gly Lys Asp Asp Gly Tyr Arg His Tyr Ala Met Asp Tyr
1               5                   10
```

<210> SEQ ID NO 25
<211> LENGTH: 16
<212> TYPE: PRT
<213> ORGANISM: Artificial Sequence
<220> FEATURE:
<223> OTHER INFORMATION: Synthetic

<400> SEQUENCE: 25

```
Arg Ser Ser Lys Ser Leu Leu His Ser Asn Ala Asn Thr Tyr Leu Tyr
1               5                   10                  15
```

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

```
Arg Met Ser Asn Leu Ala Ser
1               5
```

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

```
Met Gln His Leu Glu Tyr Pro Phe Thr
1               5

<210> SEQ ID NO 28
<211> LENGTH: 16
<212> TYPE: PRT
<213> ORGANISM: Artificial Sequence
<220> FEATURE:
<223> OTHER INFORMATION: Synthetic

<400> SEQUENCE: 28

Arg Ser Ser Lys Ser Leu Leu His Ser Asn Gly Asn Thr Tyr Leu Tyr
1               5                   10                  15

<210> SEQ ID NO 29
<211> LENGTH: 124
<212> TYPE: PRT
<213> ORGANISM: Artificial Sequence
<220> FEATURE:
<223> OTHER INFORMATION: Synthetic

<400> SEQUENCE: 29

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Pro Asn
                20                  25                  30

Ala Met Asn Trp Val Arg Gln Ala Ser Gly Lys Gly Leu Glu Trp Val
            35                  40                  45

Gly Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Gly Lys Asp Asp Gly Tyr Arg His Tyr Ala Met Asp
            100                 105                 110

Tyr Trp Gly Gln Gly Thr Thr Val Thr Val Ser Ser
        115                 120

<210> SEQ ID NO 30
<211> LENGTH: 124
<212> TYPE: PRT
<213> ORGANISM: Artificial Sequence
<220> FEATURE:
<223> OTHER INFORMATION: Synthetic

<400> SEQUENCE: 30

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Pro Asn
                20                  25                  30

Ala Met Asn Trp Val Arg Gln Ala Ser Gly Lys Gly Leu Glu Trp Val
            35                  40                  45

Gly Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95
```

Tyr Cys Val Arg Gly Lys Asp Asp Gly Tyr Arg His Tyr Ala Met Asp
            100                 105                 110

Tyr Trp Gly Gln Gly Thr Thr Val Thr Val Ser Ser
        115                 120

<210> SEQ ID NO 31
<211> LENGTH: 124
<212> TYPE: PRT
<213> ORGANISM: Artificial Sequence
<220> FEATURE:
<223> OTHER INFORMATION: Synthetic

<400> SEQUENCE: 31

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Pro Asn
            20                  25                  30

Ala Met Asn Trp Val Arg Gln Ala Ser Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Asn Leu Lys Thr Glu Asp Thr Ala Val Tyr
                85                  90                  95

Tyr Cys Val Arg Gly Lys Asp Asp Gly Tyr Arg His Tyr Ala Met Asp
            100                 105                 110

Tyr Trp Gly Gln Gly Thr Thr Val Thr Val Ser Ser
        115                 120

<210> SEQ ID NO 32
<211> LENGTH: 112
<212> TYPE: PRT
<213> ORGANISM: Artificial Sequence
<220> FEATURE:
<223> OTHER INFORMATION: Synthetic

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Synthetic

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Synthetic

<400> SEQUENCE: 34

Asp Ile Val Met Thr Gln Ala Pro Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Ala Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 35
<211> LENGTH: 5
<212> TYPE: PRT
<213> ORGANISM: Artificial Sequence
<220> FEATURE:
<223> OTHER INFORMATION: Synthetic

<400> SEQUENCE: 35

Thr Tyr Ala Met Asn
1               5

<210> SEQ ID NO 36
<211> LENGTH: 19
<212> TYPE: PRT
<213> ORGANISM: Artificial Sequence
<220> FEATURE:
<223> OTHER INFORMATION: Synthetic

<400> SEQUENCE: 36

Arg Ile Arg Ser Lys Ala Asn Asn Tyr Ala Thr Tyr Tyr Ala Asp Ser
1               5                   10                  15

Val Lys Asp

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Asp Arg Ser Arg Gly Glu Asp Tyr Ala Met Asp Tyr
1               5                   10

<210> SEQ ID NO 38
<211> LENGTH: 123
<212> TYPE: PRT
<213> ORGANISM: Artificial Sequence
<220> FEATURE:
<223> OTHER INFORMATION: Synthetic

<400> SEQUENCE: 38

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Asp Arg Ser Arg Gly Glu Asp Tyr Ala Met Asp Tyr
            100                 105                 110

Trp Gly Gln Gly Thr Leu Val Thr Val Ser Ser
        115                 120

<210> SEQ ID NO 39
<211> LENGTH: 123
<212> TYPE: PRT
<213> ORGANISM: Artificial Sequence
<220> FEATURE:
<223> OTHER INFORMATION: Synthetic

<400> SEQUENCE: 39

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg Asp Arg Ser Arg Gly Glu Asp Tyr Ala Met Asp Tyr

```
                    100                 105                 110

Trp Gly Gln Gly Thr Leu Val Thr Val Ser Ser
        115                 120

<210> SEQ ID NO 40
<211> LENGTH: 123
<212> TYPE: PRT
<213> ORGANISM: Artificial Sequence
<220> FEATURE:
<223> OTHER INFORMATION: Synthetic

<400> SEQUENCE: 40

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Ala Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Asn Leu Lys Thr Glu Asp Thr Ala Val Tyr
                85                  90                  95

Tyr Cys Val Arg Asp Arg Ser Arg Gly Glu Asp Tyr Ala Met Asp Tyr
            100                 105                 110

Trp Gly Gln Gly Thr Leu Val Thr Val Ser Ser
        115                 120

<210> SEQ ID NO 41
<211> LENGTH: 112
<212> TYPE: PRT
<213> ORGANISM: Artificial Sequence
<220> FEATURE:
<223> OTHER INFORMATION: Synthetic

<400> SEQUENCE: 41

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Synthetic

<400> SEQUENCE: 42
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65              70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110
```

<210> SEQ ID NO 43
<211> LENGTH: 112
<212> TYPE: PRT
<213> ORGANISM: Artificial Sequence
<220> FEATURE:
<223> OTHER INFORMATION: Synthetic

<400> SEQUENCE: 43

```
Asp Ile Val Met Thr Gln Ser Pro Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Ala Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65              70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110
```

<210> SEQ ID NO 44
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 44

```
Trp Gly Xaa Gly
1
```